US010046059B2

(12) United States Patent
Lee et al.

(10) Patent No.: US 10,046,059 B2
(45) Date of Patent: Aug. 14, 2018

(54) METHODS OF ADMINISTERING AN N-TERMINAL MODIFIED PEG-TRAIL

(71) Applicant: Theraly Pharmaceuticals Inc., Elkridge, MD (US)

(72) Inventors: Kang Choon Lee, Seoul (KR); Seulki Lee, Elkridge, MD (US); Eun Ji Park, Daegu (KR)

(73) Assignee: D&D Pharmatech Inc., Seongnam-si (KR)

( * ) Notice: Subject to any disclaimer, the term of this patent is extended or adjusted under 35 U.S.C. 154(b) by 0 days.

(21) Appl. No.: 15/138,109

(22) Filed: Apr. 25, 2016

(65) Prior Publication Data

US 2016/0279253 A1 Sep. 29, 2016

(51) Int. Cl.

| | | |
|---|---|---|
| *C07K 14/525* | (2006.01) | |
| *A61K 38/19* | (2006.01) | |
| *A61K 47/48* | (2006.01) | |
| *C07K 14/705* | (2006.01) | |
| *A61K 47/60* | (2017.01) | |
| *G01N 30/96* | (2006.01) | |
| *B01D 15/36* | (2006.01) | |
| *C07K 14/52* | (2006.01) | |

(52) U.S. Cl.
CPC ...... *A61K 47/48215* (2013.01); *A61K 38/191* (2013.01); *A61K 47/60* (2017.08); *C07K 14/525* (2013.01); *C07K 14/70575* (2013.01); *A61K 38/19* (2013.01); *B01D 15/361* (2013.01); *C07K 14/52* (2013.01); *C07K 2319/73* (2013.01); *G01N 30/96* (2013.01)

(58) Field of Classification Search
CPC ........ A61K 38/00; A61K 38/16; A61K 38/17; A61K 38/19; A61K 38/18; C07K 14/7151; C07K 14/52; C07K 14/47; C07K 14/521; C07K 14/4747; C07K 14/475

See application file for complete search history.

(56) References Cited

U.S. PATENT DOCUMENTS

| | | |
|---|---|---|
| 2006/0141561 A1 | 6/2006 | Kelley |
| 2011/0038855 A1 | 2/2011 | Schoenberger |
| 2012/0021995 A1 | 1/2012 | Bowdish |
| 2013/0101553 A1 | 4/2013 | Kisseleva |

FOREIGN PATENT DOCUMENTS

| | | |
|---|---|---|
| KR | 1020020010363 | 2/2002 |
| WO | 98031383 | 7/1998 |
| WO | 200069911 | 11/2000 |
| WO | WO-2004001009 A2 * | 12/2003 |
| WO | 2004022004 | 3/2004 |
| WO | 2006042848 | 4/2006 |
| WO | 2007145457 | 2/2007 |

OTHER PUBLICATIONS

Chae et al. Improved antitumor activity and tumor targeting of NH2-terminal-specific PEGylated tumor necrosis factor-related apoptosis-inducing ligand. Mol Cancer Ther 9(6): 1719-1729, 2010.*
Harith et al. On the TRAIL of obesity and diabetes. Trends Endocrinol Metabol 24(11): 578-587, 2013.*
Jiang et al. PEGylated TNF-related apoptosis-inducing ligand (TRAIL) for effective tumor combination therapy. Biomaterials 32: 8529-8537, 2011.*
Kim et al. PEGylated TNF-related apoptosis-inducing ligand (TRAIL) analogues: pharmacokinetics and antitumor effects. Bioconjugate Chem 22(8): 1631-1637, 2011.*
Martinez-Lostao et al. Targeting the Apo2L/TRAIL system for the therapy of autoimmune diseases and cancer. Biochem Pharmacol 93: 1475-1483, 2012.*
Bataller, et al., "Hepatic stellate cells as target for treatment of liver fibrosis", Semin Liver Dis, 21(03):437-52 (2001).
Bataller, et al., "Liver fibrosis", Clin. Invest., 115(2):209-18 (2005).
Beljaars, et al., "Albumin modified with mannose 6-phosphate: A potential carrier for selective delivery of antifibrotic drugs to rat and human hepatic stellate cells", Hepatology, 29:1486-93 (1999).
Beljaars, et al., "Successful targeting to rat hepatic stellate cells using albumin modified with cyclic peptides that recognize the collagen type VI receptor", J Biol Chem., 275:12743-51 (2000).
Benedict, et al., TRAIL: not just for tumors anymore J. Exp. Med., 209(11):1903-6 (2012).
Brocchini, et al., "PEGylation of native disulfide bonds in proteins", Nature protocols, 1:2241-52 (2006).
Byeon, et al., "Human serum albumin-TRAIL conjugate for the treatment of rheumatoid arthritis", Bioconjug Chem., 25(12):2212-21 (2014).
Cong, et al., "Site-specific PEGylation at histidine tags". Bioconjugate Chemistry, 23(2):248-63 (2012).
Definition of Dimer, thefreedictionary.com, 2 pages, accessed Dec. 8, 2014.
Definition of Trimer, thefreedictionary.com, 2 pages, accessed Dec. 8, 2014.

(Continued)

*Primary Examiner* — Bridget E Bunner
(74) *Attorney, Agent, or Firm* — Pabst Patent Group LLP

(57) ABSTRACT

Disclosed herein are an N-terminal modified PEG-TRAIL conjugates and methods of making and using thereof. The PEG-TAIL conjugates have bioactivity that is substantially similar to that of native TRAIL coupled with an extended in vivo half-life and enhanced stability. The disclosed PEG-TRAIL conjugates exhibit significantly reduced hepatotoxicity when compared to that of non-PEGylated trimeric TRAIL. The disclosed methods of making the PEG-TRAIL conjugates provide a homogeneous, highly pure, form of N-terminal modified PEG-TRAIL. Compared to native TRAIL, the PEG-TRAIL conjugates exhibits high solubility and solution stability. The PEG-TRAIL conjugates are useful in preventing and treating proliferative or autoimmune diseases.

11 Claims, 8 Drawing Sheets

(56) References Cited

OTHER PUBLICATIONS

European Search Report for EP 12804683 dated Nov. 20, 2014.
Fee, et al., "Size comparison between proteins PEGylated with branched and linear poly(ethylene glycol) molecules", Biotechnol Bioeng., 98(4):725-3 (2007).
Friedman, "Evolving challenges in hepatic fibrosis", Nat Rev Gastroenterol Hepatol. 7(8):425-36 (2010).
Friedman, "Fibrogenic cell reversion underlies fibrosis regression in liver", PNAS, 109(24):9230-1 (2012).
Gong, et al., "Site-specific PEGylation of exenatide analogues markedly improved their glucoregulatory activity", Br J Pharmacol., 163(2):399-412 (2011).
International Search Report and Written Opinion for PCT/US2015/020015 dated Jul. 8, 2015.
International Search Report for corresponding PCT application PCT/US2015/026513 dated Jun. 7, 2015.
Iredale, et al., "Mechanisms of spontaneous resolution of rat liver fibrosis. Hepatic stellate cell apoptosis and reduced hepatic expression of metalloproteinase inhibitors", J Clin Invest, 102(3):538-49 (1998).
Kim, et al., "The secretable form of trimeric TRAIL, a potent inducer of apoptosis", Biochem Biophys Res Comm., 321:920-35 (2004).
Kim, et al., "A sulfate polysaccharide/TNF-related apoptosis-inducing ligand (TRAIL) complex for the long-term delivery of TRAIL in poly(lactic-co-glycolic acid) (PLGA) microspheres", J Pharm Pharmacol., 65(1):11-21 (2013).
Kim, et al., "Bioimaging for targeted delivery of hyaluronic Acid derivatives to the livers in cirrhotic mice using quantum dots", ACS Nano, 4(6):3005-14 (2010b).
Kim, et al., "Ionic complex systems based on hyaluronic acid and PEGylated TNF-related apoptosis-inducing ligand for treatment of rheumatoid arthritis", Biomaterials, 31(34):9057-64 (2010a).
Kim, et al., "PEGylated TNF-related apoptosis-inducing ligand (TRAIL)-loaded sustained release PLGA microspheres for enhanced stability and antitumor activity", J Control Release, 150(1):63Ã?Â¬-9 (2011b).
Kim, et al., "Preparation and characterization of Apo2L/TNF-related apoptosis-inducing ligand-loaded human serum albumin nanoparticles with improved stability and tumor distribution", J Pharm Sci., 100(2):482-91 (2011c).
Kim, et al., "Site-specific PEGylated Exendin-4 modified with a high molecular weight trimeric PEG reduces steric hindrance and increases type 2 antidiabetic therapeutic effects", Bioconjug Chem., 23(11):2214-20 (2012).
Kinstler, et al, "Mono-N-terminal poly(ethylene glycol)-protein conjugates", Adv Drug Deliv., 54:477-85 (2002).
Lakner, et al., "Inhibitory effects of microRNA 19b in hepatic stellate cell-mediated fibrogenesis", Hepatology, 56(1):300-10 (2012).
Lee, et al., "Treatment with PEGylated TNF-related apoptosis-inducing ligand (TRAIL) induces apoptosis of human rheumatoid arthritis (RA) fibroblast-like synoviocytes (FLS) and suppresses arthritis in murine colla en-induced arthritis", Arthritis and Rheumatism; 72nd Annual scientific meeting of the American college of Rheumatology/43rd annual scientific meeting, Wiley San Francisco, CA, 58(9): Suppl S p. s539, Sep. 1, 2008.
Liao, et al., "Trail reduced joint inflammation, osteoclast activation and and loss in experimental arthritis", Allergy, 68(98):67 (2013).
Louis, et al., "Interleukin-10 controls neutrophilic infiltration, hepatocyte proliferation, and liver fibrosis induced by carbon tetrachloride in mic", Hepatology, 28:1607-15 (1998).
Ma, et al., "TNF inhibitor therapy for rheumatoid arthritis (Review)", Biomed Reports, 1(2):177-84 (2012).
Mayo Clinic, "Diabetes", www.mayoclinic.org/diseases-conditions/diabetes/in-depth/diabetes-symthoms/art, 2 pages, accessed Dec. 19, 2014.
Molineux, "The design and development of pegfilgrastim (PEG-rmetHuG-CSF, Neulasta)", Curr Pharm Des., 10(11):1235-44 (2004).
Park, et al., "Down-regulation of FoxO-dependent c-FLIP expression mediates Trail-induced apoptosis in activated hepatic stellate cells", Cell Signal., 21(10):1495-503 (2009).
Pavet, et al., "Multivalent DR5 peptides activate the TRAIL death pathway and exert tumoricidal activity", Cancer Res., 70:1101-10, (2010).
Poelstra, et al., "Drug targeting to the diseased liver", J. Control Release, 161(2):188-97 (2012).
Radaeva, et al., "Natural killer cells ameliorate liver fibrosis by killing activated stellate cells in NKG2D-dependent and tumor necrosis factor-related apoptosis-inducing ligand-dependent manners", Gastroenterology, 130(2):435-52 (2006).
Shibata, et al.,"Functionalization of tumor necrosis factor-a using phase display technique and PEGylation improves its antitumor therapeutic window",Clin Cancer Res., 10:8293-300 (2004).
Taimr, "Activated stellate cells express the TRAIL receptor-2/death receptor-5 and undergo TRAIL-mediated apoptosis", Hepathology, 37(1):89-95 (2003).
TNFSF10, symbol report, http://www.genenames.org/data/hgnc_data.php? hgnc_id=11925 , 1 page, downloaded Mar. 8, 2011.
Tur,et al., "DR4-selective tumor necrosis factor-related apoptosis-inducing ligand (TRAIL) variants obtained by structure-based design", J. Biological Chemistry, 283(29):20560-8 (2008).
van der Sloot, "Designed tumor necrosis factor-related apoptosis-inducing ligand variants initiating apoptosis exclusively via the DR5 receptor", PNAS,103(23):8634-9 (2006).
Wahl, et al., "Increased apoptosis induction in hepatocellular carcinoma by a novel tumor-targeted TRAIL fusion protein combined with bortezomib", Hepatology, 57(2):625-36 (2013).
Walczak, et al., "umoricidal activity of tumor necrosis factor-related apoptosis-inducing ligand in vivo", Nature Med., 5(2):157-63 (1999).
Wang, et al., "Small-molecule activation of the TRAIL receptor DR5 in human cancer cells", Nature Chemical Biology, 9:84-9 (2013).
Wu, et al.,"Regression of human mammary adenocarcinoma by systemic administration of a recombinant gene encoding the hFlex-TRAIL fusion protein", Mole Therapy, 3(3):368-74 (2001).
Xiang, et al.,"Tissue distribution, stability, and pharmacokinetics of APO2 ligand/tumor necrosis factor-related apoptosis-inducing ligand in human colon carcinoma COLO205 tumor-bearing nude mice", Drug Metab Dispo., 32(11):1230-8 (2004).
Yamamoto, et al., "Site-specific PEGylation of a lysine-deficient TNF-a with full bioactivity", Nature BioTech., 21:545-52 (2003).
Yang, et al., "Target specific hyaluronic acid-interferon alpha conjugate for the treatment of hepatitis C virus infection", Biomaterials, 32(33):8722-9 (2011).
Yoshioka, et al.,"Optimal site-specific PEGylation of mutant TNF-alpha improves its antitumor potency", Biochem Biophys Res Comm., 315:808-14 (2004).
Youn, et al., "Biological and physicochrmical evaluation of the conformational stability of tumor nrcrosis factor-related apoptosis-inducing ligand (TRAIL)", Biotechnol Lttrs., 29:713-21 (2007).

* cited by examiner

METHODS OF ADMINISTERING AN N-TERMINAL MODIFIED PEG-TRAIL

REFERENCE TO SEQUENCE LISTING

The Sequence Listing submitted as a text file named "THER_107_CIP_ST25.txt", created on Jul. 31, 2015, and having a size of 4,334 bytes is hereby incorporated by reference.

FIELD OF THE INVENTION

The invention is generally directed to N-terminal modified polyethylene glycol (PEG)-TRAIL conjugate and a preparation method and use thereof.

BACKGROUND OF THE INVENTION

Tumor necrosis factor (TNF)-related apoptosis-inducing ligand (TRAIL) is a typical member of the TNF family, and is a membrane protein participating in apoptosis. TRAIL is a protein consisting of 281 amino acids. The extracellular domain containing amino acids from arginine at position 114 to glycine at position 281 affects apoptosis. Three molecules of TRAIL form a structurally modified trimer. The TRAIL trimer assembles with receptors participating in cell death to induce apoptosis.

A major difference between TRAIL and other members of the TNF superfamily, such as TNF and CD95L, is their ability not to induce cell death of normal tissues. A variety of medical or pharmaceutical applications have been attempted using TNF and CD95L to induce cell death. Since TNF and CD95L proteins induce death of normal cells as well as cancer cells and over-activated immune cells, they have limited applicability. In contrast, TRAIL induces apoptosis in a wide range of cancer cells and over-activated immune cells with little effect on normal cells. This is due to the differential expression of TRAIL receptors between cell types.

Five TRAIL receptors have been identified. Among them, DR4 (TRAIL-R1) and DR5 (TRAIL-R2) are representative cell death-related receptors. When TRAIL binds to DR4 or DR5, an intracellular death domain of the receptor is activated and thus transduces apoptotic signals via various signal transduction pathways, leading to apoptotic cell death. TRAIL can also bind to DcR1, DcR2 and osteoprotegerin (OPG), which do not induce apoptosis. No marked difference has been seen in the expression levels of the cell death-inducing receptors DR4 and DR5 between normal and tumor cells. In contrast, the three other receptors not inducing apoptosis are expressed at high levels in normal cells, but are either expressed at low levels or are not expressed at all in tumor cells. Thus, in normal cells, TRAIL binds mostly to DcR1, DcR2 and OPG, which do not contain a death domain, and thereby do not induce cell death. In contrast, in cancer cells and over-activated immune cells, apoptosis is induced by the binding of TRAIL to DR4 and DR5, which contain a death domain. Such selective apoptosis induction of TRAIL seems to be a particularly attractive feature in medical or pharmaceutical applications.

TRAIL-mediated apoptosis has been observed in various types of cancer cells, including colon carcinoma, glioma, lung carcinoma, prostate carcinoma, brain tumors and multiple myeloma cells. TRAIL has been proven to have very high anticancer activity in animals. The good anticancer efficacy of TRAIL has been obtained through the use of TRAIL alone, as well as in combination with other anticancer agents, such as paclitaxel and doxorubicin, and radiotherapy. Clinical trials are currently being conducted by Genentech and Amgen using TRAIL, which has good anticancer efficacy in solid tumors. In addition to cancer, various approaches using TRAIL have been made in arthritis, an autoimmune disease, for relieving and treating arthropathy by inducing the death of overactivated immune cells. In addition to protein therapy, gene therapy has been attempted through the delivery of the TRAIL gene. TRAIL may also be useful in the treatment of T cell-mediated autoimmune disorders such as experimental autoimmune encephalomyelitis, rheumatoid arthritis and type I diabetes.

However, native TRAIL has some problems as a therapeutic. The major problem is the low trimer formation ratio of native TRAIL. TRAIL monomers do not bind to the TRAIL receptors, and thus do not induce apoptosis. In this regard, many studies have been performed with the goal of improving the trimeric structure and trimer formation ratio of TRAIL. The zinc ion has been known to play a critical role in trimerization of native TRAIL. Mutants of TRAIL have been developed based on computer analysis results. For the formation of TRAIL trimers, the most useful method appears to be the introduction of an amino acid sequence favoring trimeric folding. Such sequences include a leucine zipper motif and an isoleucine zipper motif. Henning Walczak reported the anticancer efficacy of a trimeric TRAIL derivative in which a leucine zipper motif is added to the N terminus of native TRAIL (Walczak et al., *Nature Medicine*, 5:157-163 (1999)). Seol reported a TRAIL derivative containing a novel isoleucine zipper motif and having good apoptotic activity (Kim et al., *BBRC*, 321:930-935 (2004)).

Another problem in the clinical applications of TRAIL involves cytotoxicity shown in normal cells of some tissues. Most normal cells are resistant to cytotoxicity, resulting from the expression of the various TRAIL receptors, but some hepatocytes and keratinocytes are sensitive to TRAIL-mediated cytotoxicity (Yagita et al., *Cancer Sci.*, 95:777-783 (2004); Jo et al., *Nature Medicine*, 6:564-567 (2000); Zheng et al., *J. Clin. Invest.*, 113:58-64 (2004)).

TRAIL also has a short half-life in vivo, which should be overcome for the successful clinical application of TRAIL. TRAIL has different half-lives according to the species of animals used in tests. For example, TRAIL has been reported to have a half-life of several minutes in rodents and about 30 minutes in apes (Xiang, et al., *Drug Metabolism and Disposition*, 32:1230-1238 (2004)). Most TRAIL is rapidly excreted via the kidneys. This short half-life is considered a drawback to the pharmaceutical usefulness of TRAIL, resulting in a need for TRAIL or derivatives thereof having an extended half-life. Other problems to be solved include the low solubility and solution stability of TRAIL.

There remains a need for biologically active, highly pure TRAIL conjugates that retain biological activity of native TRAIL having a prolonged serum half-life, increased solubility and which are not cytotoxic to healthy cells.

SUMMARY OF THE INVENTION

N-terminal modified PEG-TRAIL conjugates in which PEG, or a PEG derivative, is bound to the N-terminus of TRAIL, and methods of making the N-terminal modified PEG-TRAIL conjugates, have been developed. Also provided are methods of using the N-terminal modified PEG-TRAIL conjugates. The PEGylated TRAIL conjugates are suitable for preventing or treating proliferative and autoimmune diseases.

In some embodiments, the N-terminal modified PEG-TRAIL conjugate is a trimeric TRAIL containing zipper amino acid motifs present at the N-terminus of each TRAIL monomer, and a PEG or a derivative thereof. In this embodiment, one or more PEG is directly or indirectly bound to the N-terminal domain of a monomer of the trimeric TRAIL, and has a molecular weight of between 1,000 and 100,000 Dalton as determined by SDS-PAGE.

In some embodiments, the PEG, or the derivative thereof is linear. In other embodiments, the PEG, or the derivative thereof is branched. In some embodiments, the PEG or the derivative thereof has a molecular weight between 5,000 and 30,000 Daltons, or between 10,000 and 50,000 Daltons, as determined by SDS-PAGE. In preferred embodiments, the PEG is bound to the TRAIL monomer via an N-terminal amino acid residue of the monomer of the trimeric TRAIL.

Typically, the PEG derivative is methoxypolyethylene glycol succinimidyl propionate, methoxypolyethylene glycol N-hydroxysuccinimide, methoxypolyethylene glycol aldehyde, methoxypolyethylene glycol maleimide and multiple-branched polyethylene glycol. In preferred embodiments, the PEG or the derivative thereof is methoxypolyethylene glycol aldehyde.

Typically, each TRAIL monomer in the trimeric TRAIL in the PEG-TRAIL conjugate is human TRAIL, having an amino acid sequence 281 amino acids in length (SEQ ID NO: 1). In preferred embodiments, each TRAIL monomer in the trimeric TRAIL in the PEG-TRAIL conjugate has an amino acid sequence from arginine-114 to glycine-281 of the human TRAIL (SEQ ID NO: 2).

In preferred embodiments, the zipper amino acid motif is an isoleucine zipper.

An N-terminal modified PEG-TRAIL conjugate has higher solubility and stability and increased in vivo half-life when compared to native TRAIL, while at the same time has a biological activity similar to that of native TRAIL.

The pegylation reduces TRAIL uptake and removal by hepatocytes and the hepatic reticuloendothelial system, leading to a decrease in TRAIL-mediated hepatoxicity, and improves pharmacokinetic profiles of a TRAIL with long-term storage, thereby reducing TRAIL's administration frequencies and allowing sustained duration of effects of the TRAIL.

Methods of making the mono-PEGylated N-terminal modified PEG-TRAIL produce the mono-PEGylated N-terminal modified PEG-TRAIL as the single PEGylated TRAIL species of the reaction mixture. In some embodiments, the mono-PEGylated N-terminal modified PEG-TRAIL is isolated from the reaction mixture using size exclusion chromatography. In other embodiments, the mono-PEGylated N-terminal modified PEG-TRAIL is purified from the reaction mixture using ion exchange chromatography.

The pegylated TRAIL is useful at preventing or treating proliferative or autoimmune diseases. The methods generally include administering to a subject in need of treatment a pharmaceutically effective amount of the mono-PEGylated N-terminal modified PEG-TRAIL. Cancers to be prevented or treated include colon carcinoma, glioma, lung carcinoma, prostate carcinoma, brain tumor and multiple myeloma. In some embodiments, the autoimmune disease to be prevented or treated is lupus (experimental autoimmune encephalomyelitis), rheumatoid arthritis or type I diabetes.

DETAILED DESCRIPTION OF THE INVENTION

I. Definitions

Figure 1:
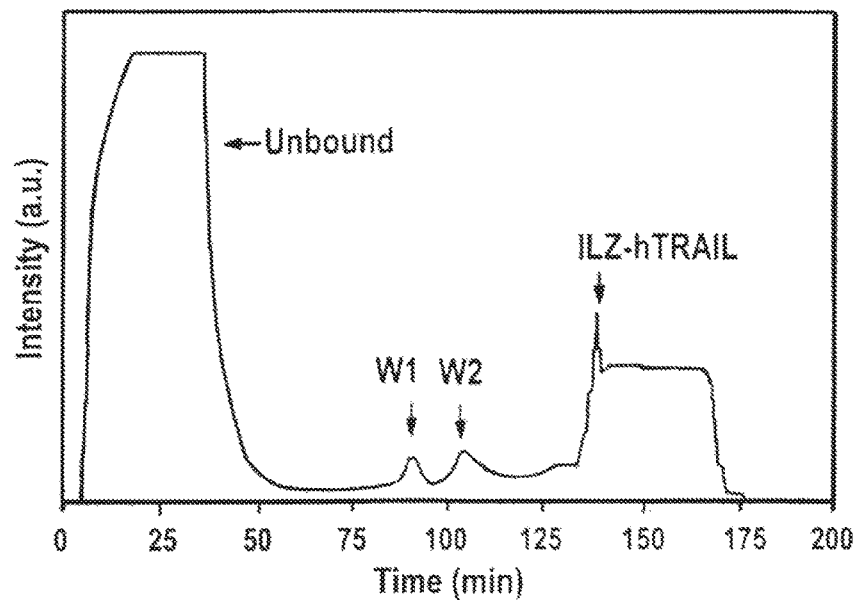
FIG. 1 is a chromatogram of the recombinant hTRAIL purified through Ni-affinity chromatography (washing 1 (w1): washing with 10 mM imidazole-containing phosphate buffer; washing 2 (w2): washing with 50 mM imidazole-containing phosphate buffer).

As used herein, the term "effective agent" or "biologically active agent" are used interchangeably herein to refer to a chemical or biological compound that induces a desired pharmacological and/or physiological effect, wherein the effect may be prophylactic or therapeutic. The terms also encompass pharmaceutically acceptable, pharmacologically active derivatives of those active agents specifically mentioned herein, including, but not limited to, salts, esters, amides, prodrugs, active metabolites, analogs and the like. When the terms "active agent," "pharmacologically active agent" and "drug" are used, then, it is to be understood that the disclosure includes the active agent per se as well as pharmaceutically acceptable, pharmacologically active salts, esters, amides, prodrugs, metabolites, analogs etc.

As used herein, the term "N-terminal modified" refers to modification of a protein or peptide at its amino (N)-terminus. For example, if the modification is PEGylation, then the PEG moiety is added/linked/conjugated at one or more amino acid residues forming the first quarter of the peptide at the N-terminus. The amino acid residues include, but are not limited to, lysine, cysteine, serine, tyrosine, histidine, phenylalanine, or arginine.

As used herein, the term "branched" refers to a structure of a polymeric molecule, wherein the polymeric molecule is a linear polymer serving as a backbone or main chain with branches of the same basic polymer, or another polymer, extending from the main chain. This structure can be represented by monomers polymerized into linear stretches and two or more of the linear stretches of the polymeric molecule connected at one end to one or more functional groups of a small molecule, wherein the small molecule has a molecular weight of less than 1000 Dalton. Examples of branched polymeric molecules, such as branched PEG, are presented in Roberts et al., *Advanced Drug Delivery Reviews*, 54:459-476 (2002). Exemplary small molecules with functional groups include N-hydroxysuccinimide, maleimide, glycerine, pentaerythritol, or hexaglycerine.

As used herein, the term "stability" or "solution stability" refers to the stability of a molecule, over time, in solution. The molecule is considered stable in solution when the molecule exhibits no precipitation, or falling out of solution, upon storage over time. The time period may range from minutes, to days, weeks, months, or years. For example, the molecule may exhibit stability in solution for a period of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more days, or for a period of months or years, during which up to about 70%, up to about 75%, up to about 80%, up to about 85%, up to about 90%, up to about 95%, or up to about 99% of the starting amount of the molecule remains in solution.

As used herein, the term "pure" or "purified" refers to the purity of a molecule in solution. As referred to the N-terminal modified PEG-TRAIL conjugates, the term refers to solutions containing N-terminal modified PEG-TRAIL conjugates, wherein up to about 80%, up to about 85%, up to about 90%, up to about 95%, or up to about 99% of the conjugates are trimeric TRAIL molecules PEGylated with only one PEG moiety at the N-terminal amino acid of one of the TRAIL monomers in the TRAIL trimer.

As used herein, the term "hepatotoxicity" refers to cytotoxicity as related to hepatocytes.

As used herein, the term "therapeutically effective amount", or "pharmaceutically effective amount" means an amount of a therapeutic, prophylactic, and/or diagnostic agent that is sufficient, when administered to a subject suffering from or susceptible to a disease, disorder, and/or condition, to treat, alleviate, ameliorate, relieve symptoms of, prevent, delay onset of, inhibit progression of, reduce severity of, and/or reduce incidence of the disease, disorder, and/or condition.

As used herein, the term "treating" refers to partially or completely alleviating, ameliorating, relieving, delaying onset of, inhibiting progression of, reducing severity of, and/or reducing incidence of one or more symptoms or features of a particular disease, disorder, and/or condition. For example, "treating" cancer may refer to inhibiting survival, growth, and/or spread of the cancer. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

As used herein, the term "excipient", or "pharmaceutically acceptable excipient", refers to a pharmacologically inactive substance added to the composition to further facilitate administration of the composition. Examples, without limitation, of pharmaceutically acceptable excipients include calcium carbonate, calcium phosphate, various diluents, various sugars and types of starch, cellulose derivatives, gelatin, vegetable oils and polyethylene glycols.

As used herein, the term "subject" refers to a subject, such as a vertebrate animal, preferably a mammal.

Use of the term "about" is intended to describe values either above or below the stated value in a range of approximately +/−10%; in other embodiments the values may range in value either above or below the stated value in a range of approximately +/−5%; in other embodiments the values may range in value either above or below the stated value in a range of approximately +/−2%; in other embodiments the values may range in value either above or below the stated value in a range of approximately +/−1%. The preceding ranges are intended to be made clear by context, and no further limitation is implied. All methods can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

II. Formulations

Disclosure provides an N-terminal modified PEG-TRAIL conjugate, or a pharmaceutically acceptable salt thereof, as the effective agent in a pharmaceutical formulation.

A. Effective Agent

Typically, the effective agent is full length human TRAIL in trimeric form, truncated human TRAIL in trimeric form, or TRAIL analogues. In preferred embodiments, the effective agent is a homotrimeric TRAIL formed of monomers having the amino acid sequence of SEQ ID NO: 2.

1. TRAIL
   a. Full Length and Truncated TRAIL

TRAIL may be obtained in a native or genetically engineered (recombinant) form. TRAIL may include a zipper amino acid motif favoring trimer formation and/or a terminal group facilitating isolation and purification thereof.

TRAIL is in the human form, which has an amino acid sequence of 281 amino acids in length, SEQ ID NO: 1:

MAMMEVQGGPSLGQTCVLIVIFTVLLQSLCVAVTYVYFTNELKQMQDKYS

KSGIACFLKEDDSYWDPNDEESMNSPCWQVKWQLRQLVRKMILRTSEETI

STVQEKQQNISPLVRERGPQRVAAHITGTRGRSNTLSSPNSKNEKALGRK

INSWESSRSGHSFLSNLHLRNGELVIHEKGFYYIYSQTYFRFQEEIKENT

KNDKQMVQYIYKYTSYPDPILLMKSARNSCWSKDAEYGLYSIYQGGIFEL

KENDRIFVSVTNEHLIDMDHEASFFGAFLVG.

In preferred embodiments, TRAIL has an amino acid sequence from arginine-114 (Arg, R) to glycine-281 (Gly, G) of the full-length human form (1-281), and has an amino acid sequence of SEQ ID NO: 2:

RERGPQRVAAHITGTRGRSNTLSSPNSKNEKALGRKINSWESSRSGHSFL

SNLHLRNGELVIHEKGFYYTYSQTYFREQEEIKENTKNDKQMVQYIYKYT

SYPDPILLMKSARNSCWSKDAEYGLYSIYQGGIFELKENDRIFVSVTNEH

LIDMDHEASFFGAFLVG.

Typically, TRAIL is modified with ethylene glycol (EG) units, more preferably 2 or more EG units (i.e., polyethylene glycol (PEG)) at an N-terminal amino acid residue. The N-terminal amino acid residue includes, but is not limited to, lysine, cysteine, serine, tyrosine, histidine, phenylalanine, or arginine. For example, in the SEQ ID NO: 1, the amino acid residue modified by PEG moiety may be any one of the N-terminal lysine, cysteine, serine, tyrosine, histidine, phenylalanine, or arginine. In the SEQ ID NO: 2, the amino acid residue modified by PEG moiety is the first arginine (R, Arg).

b. TRAIL Analogues

Typically, any TRAIL analogue may be suitable for PEGylation. The analogues are trimeric TRAIL wherein at least one of the three monomers has an amino acid sequence of SEQ ID NOS: 1 or 2, with one or more amino acid substitutions or deletions. The TRAIL analogues may be generated in vitro using routine molecular biology techniques.

2. Zipper Motif

TRAIL may be attached to a leucine or an isoleucine zipper (ILZ) at its N-terminus. In preferred embodiments, the zipper motif is an isoleucine zipper (Kim et al., *BBRC*, 321:930-935 (2004)).

3. PEG and its Derivatives

Polyethylene glycol (PEG) is a polymer having a structure of HO—(—CH$_2$CH$_2$O—)$_n$—H. Due to its high hydrophilicity, the molecular weight of PEG, capable of being linked to proteins with very low toxicity, ranges from about 1,000 to 100,000. PEG having a molecular weight between 1,000 and 6,000 distributes widely throughout the entire body and is metabolized via the kidney. PEG having a molecular weight of 40,000 is distributed in the blood and organs, including the liver, and is metabolized in the liver.

In general, medically and pharmaceutically useful proteins administered via parenteral routes are disadvantageous in terms of being immunogenic in the body, being poorly water-soluble and being cleared from circulation within a short period of time. Many studies have been performed to overcome such problems. U.S. Pat. No. 4,179,337 mentions that, when used as therapeutics, pegylated proteins and enzymes have effects including reduced immunogenicity, increased solubility and extended in vivo residence time, however, many also exhibit decreased bioactivity. U.S. Pat. Nos. 4,766,106 and 4,917,888 describes the conjugation of proteins to a polymer including PEG to increase the water solubility thereof. U.S. Pat. No. 4,902,502 describes the conjugation of recombinant proteins to PEG or other polymers to reduce immunogenicity and extend circulating in vivo half-life.

PEG is typically conjugated to a target protein through covalent bonding to one or more free lysine (Lys) or cysteine residues. If PEG is bound to a region directly associated with protein activity among surface regions of the protein, the PEG-attached region loses biological functions, leading to decreased protein activity. Also, since the attachment of PEG to lysine residues mostly occurs in a random manner, various kinds of PEG-protein conjugates, corresponding to particular attachment sites, exist as a mixture. From this mixture, a desired conjugate is difficult to purify and isolate.

Native TRAIL has eleven lysine residues, some of which participate in the interaction between TRAIL and its cognate receptors or are within an active site. Thus, the addition of polyethylene glycol molecules through the reaction with lysine residues may act as a very important inhibitory factor against the bioactivity of TRAIL. In the case of the TNF superfamily, several studies have noted that the bonding between lysine residues and polyethylene glycol molecules inhibits activation (Yamamoto et al., *Nature Biotechnology*, 21:546-552 (2003); Shibata et al., *Clin. Cancer Res.*, 10:8293-8300 (2004)).

TRAIL or TRAIL variants conjugated to molecules other than PEG, such as synthetic or natural water-soluble biocompatible polymers such as polyethylene oxide, polyvinyl alcohol, polyacrylamide, polysialic acid, proteins such as hyaluronic acid and chondroitin sulfate, recombinant polypeptide such as XTEN™, celluloses such as hydroxymethyl cellulose, and polyhydroxyalkyl (meth)acrylates, as well as other polysaccharides and nanoparticles, are also contemplated.

Studies show that the pharmacokinetic and pharmacodynamic profiles of TRAIL can be improved using PEGylation (Kim, et al., *Bioconjugate Chem.*, 22 (8), pp 1631-1637 (2011)). Studies show that TRAIL analogues derivatized with PEG maintain anti-cancer activity, while also exhibiting higher metabolic stabilities in plasma, extended pharmacokinetic profiles, and greater circulating half-lives (Chae, et al., *Molecular cancer therapeutics* 9(6):1719-29 (2010); Kim, et al., *Bioconjugate chemistry*, 22(8):1631-7 (2011); Kim, et al., *Journal of pharmaceutical sciences* 100(2):482-91 (2011); Kim, et al., *Journal of controlled release: official journal of the Controlled Release Society* 150(1):63-9 (2011)).

The TRAIL domain is derivatized with one or more ethylene glycol (EG) units, more preferably 2 or more EG units (i.e., polyethylene glycol (PEG)), or a derivative thereof. Derivatives of PEG include, but are not limited to, methoxypolyethylene glycol succinimidyl propionate, methoxypolyethylene glycol N-hydroxysuccinimide, methoxypolyethylene glycol aldehyde, methoxypolyethylene glycol maleimide, multiple-branched polyethylene glycol, and polyethylene glycol-polypropylene block copolymer such as a poloxamers, e.g., PLURONIC® with the following general formula:

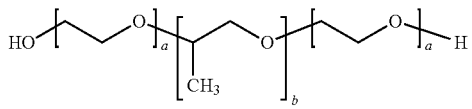

wherein
a is an integer selected from 1-200, and
b is an integer selected from 10-100.

The precise number of EG or derivative units depends on the desired activity, plasma stability, and pharmacokinetic profile. For example, Kim, et al. (supra) reported that 2, 5, 10, 20, and 30K-PEG-TRAIL resulted in greater circulating half-lives of 3.9, 5.3, 6.2, 12.3, and 17.7 h respectively in mice, versus 1.1 h for TRAIL. PEG molecule(s) conjugated to N-terminal of trimeric TRAIL may include 1, 2 or 3 PEG molecules conjugated to N-terminal of trimeric TRAIL, i.e., one PEG molecule for each of the three monomers in the trimeric TRAIL.

The TRAIL-PEG conjugates may be depicted by the following formula:

$$X\text{-}L\text{-}(PEG)_n,$$

wherein
X represents a trimeric TRAIL protein,
L represents a linker,
PEG represents a branched poly(ethylene glycol) chain, and
n is an integer selected from 2, 3, 4, 5, 6, 7 or 8.

In certain embodiments, n is 2.

The polyalkylene oxide is coupled to the protein via a linker. The linker may be a polyakylene oxide, and preferably connects two polyalkylene oxide polymers to the protein.

In a particular embodiment, the TRAIL-conjugate is a PEG-conjugate that includes a TRAIL domain including a truncated form of human TRAIL, for example, from arginine-114 to glycine-281 (SEQ ID NO: 2) of the full-length form (1-281) of human TRAIL (SEQ ID NO: 1), and PEG having a molecular weight between 1,000 and 100,000 Daltons, and preferably between 5,000 and 50,000 Daltons.

N-terminal modified PEG-TRAIL conjugates can be obtained by reacting an N-terminal amine of the TRAIL domain with an aldehyde group of the PEG in the presence of a reducing agent. PEG and TRAIL can be reacted at a molar ratio (PEG/TRAIL) of 2 to 10, or preferably 5 to 7.5.

In preferred embodiments, the TRAIL-conjugate includes a zipper amino acid motif at the N-terminus human TRAIL, for example, an isoleucine zipper motif, that allows for trimer formation between three TRAIL-conjugate monomers.

The PEG chains are preferably, but not necessarily, of equal molecular weight. Exemplary molecular weight ranges for each PEG chain is between about 10 kDa and 60 kDa, and preferably about 20 kDa and 40 kDa. PEG40 is a branched PEG moiety was synthesized and has a molecular weight of 40 kDa: 20+20 kDa (each PEG chain).

A trimeric PEG moiety can consist of a branched PEG chain attached to a linker arm. A visual description of the trimer PEG moiety is provided immediately below.

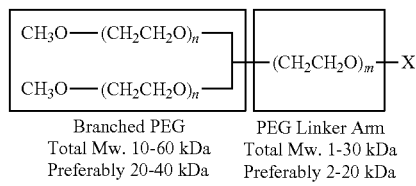

Branched PEG
Total Mw. 10-60 kDa
Preferably 20-40 kDa

PEG Linker Arm
Total Mw. 1-30 kDa
Preferably 2-20 kDa

The following trimeric PEGs were: YPEG42, YPEG43.5, YPEG45, YPEG50 and YPEG60.

YPEG42 is a trimeric PEG moiety which has a molecular weight of 42 kDa: (20+20 kDa) (branched PEG)+2 kDa (linker arm).

YPEG43.5 is a trimeric PEG moiety which has a molecular weight of 43.5 kDa: (20+20 kDa) (branched PEG)+3.5 kDa (linker arm).

YPEG45 is a trimeric PEG moiety which has a molecular weight of 45 kDa: (20+20 kDa) (branched PEG)+5 kDa (linker arm).

YPEG50 is a trimeric PEG moiety which has a molecular weight of 50 kDa: (20+20 kDa) (branched PEG)+10 kDa (linker arm).

YPEG60 is a trimeric PEG moiety which has a molecular weight of 60 kDa: (20+20 kDa) (branched PEG)+20 kDa (linker arm).

a. Linker Moiety

The protein or peptide is covalently joined to the branched PEG moiety via a linker. The linker is a polymer, and generally has an atomic length of at least 800 angstroms. Typically, the linker has an atomic length from about 800 to about 2,000 angstrom, from about 800 to about 1,500 angstrom, from about 800 to about 1,000 angstrom, or from about 900 to about 1,000 angstrom. It is to be appreciated that the atomic distances listed above refer to fully extended polymers, and that when in the solid state or solution the linker may fold or curl in ways such that the actual distance between the branched PEG and protein or peptide is less than the atomic lengths listed above.

In certain embodiments, the linker is a poly(ethylene glycol) derivative with a molecular weight between about 1 kDa to 30 kDa, preferably from about 2 kDa to 20 kDa. A linker may also be a natural or unnatural amino acid of at least 80 units in length.

PEG alternatives for the linker include synthetic or natural water-soluble biocompatible polymers such as polyethylene oxide, polyvinyl alcohol, polyacrylamide, proteins such as hyaluronic acid and chondroitin sulfate, celluloses such as hydroxymethyl cellulose, polyvinyl alcohol, and polyhydroxyalkyl (meth)acrylates.

Proteins and peptides may be covalently bound to the linker using conventional chemistries. Primary amine groups, such as found at the N-terminus or in lysine residues, will react with aldehydes and their equivalents under reductive conditions to give amines. (Molineux, *Current pharmaceutical design*, 10(11):1235-1244 (2004)). Mercapto (—SH) groups, such as found in cysteine residues, can undergo a conjugate addition with a variety of Michael acceptors, including acrylic and methacrylic acid derivatives, as well as maleimides (Gong et al., *British Journal of Pharmacology*, 163(2):399-412 (2011)). Other suitable nucleophilic groups found in peptides and proteins include disulfide bonds (Brocchini, et al., *Nature protocols*, 1:2241-2252 (2006)) and histidine residues (Cong, et al., *Bioconjugate Chemistry*, 23(2):248-263 (2012)).

The linker may be covalently joined to the protein or peptide using conventional chemistries. For instance, the linker polymer may be derivatized at one end with an electrophilic group such as an aldehyde, epoxide, halogen (chlorine, bromide, iodine), sulfonate ester (tosylate, mesylate), Michael acceptor, or activated carboxylates and then reacted with a nucleophilic amine or thiol group in the protein or peptide. Suitable Michael acceptors include acylic and methacrylic acid derivatives such as acrylamides, methacrylamides, acrylates and methacrylates, as well as maleimides. Suitable activated carboxylates include nitrophenyl carbonate and NHS (N-hydroxy succinate) esters. In other embodiments, peptides and proteins containing arginine residues may be covalently joined with a linker containing a reactive 1,3 diketone functional group.

The conjugates may be prepared by first joining the linker with the peptide or protein, followed by joining the linker with the branched poly(ethylene glycol), or by first joining the linker with the branched poly(ethylene glycol), followed by joining the linker with the peptide or protein. The optimal sequence of bond formation is determined by the specific chemical transformations involved.

B. Excipients.

1. Excipients for Parenteral Delivery

In the formulation, diluents or excipients may be used, and are exemplified by fillers, thickeners, binders, humectants, disintegrators and surfactants. Examples of solid formulations for oral administration include tablets, pills, powders, granules and capsules. The solid formulations may include, in addition to the PEG-TRAIL conjugate, at least one excipient selected from among starch, calcium carbonate, sucrose, lactose, gelatin, etc. Also, the solid formulations may include, in addition to a simple excipient, a lubricant such as magnesium stearate or talc. Examples of liquid formulations for oral administration include suspensions, internal solutions, emulsions and syrups.

The liquid formulations may include, in addition to commonly used simple diluents such as water and liquid paraffin, various excipients, which are exemplified by humectants, sweeteners, aromatics and preservatives. Examples of preparations for parenteral administration include sterile aqueous solutions, non-aqueous solutions, suspensions, emulsions, freeze-dried preparations and suppositories. In the formulation into non-aqueous solutions and suspensions, propylene glycol, PEG, vegetable oils such as olive oil, and injectable esters such as ethyl oleate may be used. A formulation may be supplemented with calcium or vitamin D3 in order to enhance its efficacy as a therapeutic agent for proliferative diseases or autoimmune diseases.

Pharmaceutical compositions may be formulated in a conventional manner using one or more physiologically acceptable carriers containing excipients and auxiliaries which facilitate processing of the active compounds into preparations which can be used pharmaceutically. Formulation of drugs is discussed in, for example, Hoover, John E., Remington's Pharmaceutical Sciences, Mack Publishing Co., Easton, Pa. (1975), and Liberman, H. A. and Lachman, L., Eds., Pharmaceutical Dosage Forms, Marcel Decker, New York, N.Y. (1980).

In the preferred embodiment, one or more solubilizing agents are included with the insulin to promote rapid dissolution in aqueous media. Suitable solubilizing agents include wetting agents such as polysorbates, glycerin and poloxamers, non-ionic and ionic surfactants, food acids and bases (e.g. sodium bicarbonate), and alcohols, and buffer salts for pH control. In a preferred embodiment the pH is adjusted using hydrochloric acid (HCL) or sodium hydroxide (NaOH). The pH of the injectable formulation is typically between about 6.9-7.4, preferably about 7.0.

Stabilizers are used to inhibit or retard drug decomposition reactions which include, by way of example, oxidative reactions. A number of stabilizers may be used. Suitable stabilizers include polysaccharides, such as cellulose and cellulose derivatives, and simple alcohols, such as glycerol (or glycerin, or glycerin); bacteriostatic agents such as phenol, benzyl alcohol, meta-cresol (m-cresol) and methylparaben; isotonic agents, such as sodium chloride, glycerol (or glycerin, or glycerine), and glucose; lecithins, such as example natural lecithins (e.g. egg yolk lecithin or soya bean lecithin) and synthetic or semisynthetic lecithins (e.g. dimyristoylphosphatidylcholine, dipalmitoylphosphatidylcholine or distearoyl-phosphatidylcholine; phosphatidic acids; phosphatidylethanolamines; phosphatidylserines such as distearoyl-phosphatidylserine, dipalmitoylphosphatidylserine and diarachidoylphospahtidylserine; phosphatidylglycerols; phosphatidylinositols; cardiolipins; sphingomyelins.

In one example, the stabilizer may be a combination of glycerol, bacteriostatic agents and isotonic agents. The most preferred formulations include glycerine and m-cresol.

2. Excipients for Oral Delivery

The formulations can be formulated for oral administration. As would be appreciated by one of skill in this art, the one or more excipients and/or carriers may be chosen based on the dosage form to be administered, the active agents being delivered, etc.

Suitable excipients include surfactants, emulsifiers, emulsion stabilizers, anti-oxidants, emollients, humectants, chelating agents, suspending agents, thickening agents, occlusive agents, preservatives, stabilizing agents, pH modifying agents, solubilizing agents, solvents, flavoring agents, colorants, fragrances, and other excipients.

C. Sensitizing Agents

Sensitizing agents may be added to formulations to increase cellular sensitivity/reduce resistance to the N-terminal modifeid mono-PEGylated PEG-TRAIL conjugates. Examples of sensitizers includes, but is not limited to, chemotherapeutic drugs, such as gemcitabine, irinotecan, doxorubicin, 5-FU and platinum-based agents such as cisplatin have been shown to synergize with TRAIL, bortezomib, and Smac mimetics, and anti-inflammatory agents, such as steroids, including methyl prednisone, dexamethasone, non-steroidal anti-inflammatory agents, including COX-2 inhibitors, corticosteroid anti-inflammatory agents, gold compound anti-inflammatory agents, immunosuppressive anti-inflammatory and anti-angiogenic agents, salicylate anti-inflammatory agents, ranibizumab, minocycline, anti-VEGF agents, including aflibercept, and rapamycin (Lemke et al., *Cell Death and Differentiation*, 21:1350-1364 (2014)).

III. Methods of Making

In another aspect, a method of making and using the N-terminal modified PEG-TRAIL conjugate has been developed.

A. PEGylation

Any suitable method of PEGylation may be used. In preferred embodiments, the method allows PEGylation of only one of the TRAIL monomers at only one amino acid present at the N-terminus of the protein. Examples of different protein PEGylation strategies are presented by Roberts and colleagues (Roberts et al, *Advanced Drug Delivery Reviews*, 54:459-476 (2002)).

The preferred method is as follows. The N-terminal modified PEG-TRAIL conjugate may be obtained by reacting an N-terminal amine of TRAIL with an aldehyde group of PEG in the presence of a reducing agent. In the present method, PEG and TRAIL react at a molar ratio (PEG/TRAIL) of 2 to 10, and preferably 5 to 7.5. The reducing agent may include $NaCNBH_3$ and $NaBH_4$.

B. Purification

The N-terminal modified mono-PEGylated TRAIL conjugates can be purified with any suitable method. Preferably, the method is size exclusion chromatography (SEC), or ion exchange chromatography (IEX).

1. Size-Exclusion Chromatography

During size-exclusion chromatography (SEC) molecules in solution are separated by their size, and in some cases molecular weight. The advantages of this method include good separation of large molecules from the small molecules with a minimal volume of eluate, and that various solutions can be applied without interfering with the filtration process, all while preserving the biological activity of the particles to be separated. With size exclusion chromatography, there are short and well-defined separation times and narrow bands, which lead to good sensitivity. There is also no sample loss because solutes do not interact with the stationary phase. Disadvantages are, for example, that only a limited number of separations can be accommodated because the time scale of the chromatogram is short, and, in general, there has to be a 10% difference in molecular mass to have a good resolution.

SEC is usually achieved with an apparatus called a column, which consists of a hollow tube tightly packed with extremely small porous polymer beads designed to have pores of different sizes. These pores may be depressions on the surface or channels through the bead. As the solution travels down the column some particles enter into the pores. Larger particles cannot enter into as many pores. The larger the particles, the faster the elution. The filtered solution that is collected at the end is known as the eluate. The void volume includes any particles too large to enter the medium, and the solvent volume is known as the column volume. The eluent is collected in constant volumes, known as fractions. The more similar the particles are in size the more likely they will be in the same fraction and not detected separately. More advanced columns overcome this problem by constantly monitoring the eluent.

The collected fractions are often examined by spectroscopic techniques to determine the concentration of the particles eluted. Common spectroscopy detection techniques are refractive index (RI) and ultraviolet (UV). When eluting spectroscopically similar species (such as during biological purification), other techniques may be necessary to identify the contents of each fraction.

2. Ion Exchange Chromatography

Ion exchange chromatography allows the separation of ions and polar molecules based on their affinity to the ion exchanger. It can be used for almost any kind of charged molecule including large proteins, small nucleotides and amino acids.

Ion-exchange chromatography retains analyte molecules on the column based on coulombic (ionic) interactions. The stationary phase surface displays ionic functional groups that interact with analyte ions of opposite charge. This type of chromatography is further subdivided into cation exchange chromatography and anion-exchange chromatography. The ionic compound consisting of the cationic species and the anionic species can be retained by the stationary phase.

Cation exchange chromatography retains positively charged cations because the stationary phase displays a negatively charged functional group. Anion exchange chromatography retains anions using positively charged functional group. The ion strength of either cations or anions in the mobile phase can be adjusted to shift the equilibrium position, thus retention time.

Ion exchange chromatography separates proteins with regards to their net charge, which is dependent on the composition of the mobile phase. By adjusting the pH or the ionic concentration of the mobile phase, various protein molecules can be separated. For example, if a protein has a net positive charge at pH 7, then it will bind to a column of negatively charged beads, whereas a negatively charged protein would not. By changing the pH so that the net charge on the protein is negative, it too will be eluted.

C. Methods of Making Formulations

Following purification, the N-terminal PEGylated PEG-TRAIL conjugates may be included into liquid or solid formulations for oral or parenteral administration, in single or multiple dosage units. Typically, the formulation will include an N-terminal PEGylated PEG-TRAIL conjugate, and one or more excipients for oral or parenteral delivery. Generally, the formulations contain a pharmaceutically effective amount of the N-terminal PEGylated PEG-TRAIL conjugates.

Methods of making liquid or solid formulation for oral or parenteral administration are known in the art. The methods are presented in "Handbook of Pharmaceutical Manufacturing Formulations", 2nd ed., vol. 1-3, Niazi S. K., Informa Healthcare, New York, N.Y., 2009.

IV. Methods of Use

Methods of using the N-terminal PEGylated PEG-TRAIL conjugates for preventing or treating a disease, in which a solid or liquid formulation of an N-terminal PEGylated PEG-TRAIL conjugate, containing a pharmaceutically effective amount of the conjugate, is administered to a subject in need thereof.

Following administration, the state, symptoms, or manifestations, of the disease are typically monitored by the subject and the treating physician. In preferred embodiments, administration of the formulation reduces, partially or completely, the severity of one or more symptoms, or manifestations, of the disease is when compared to the severity of the symptoms prior to administration. This reduction in symptom severity alleviates, ameliorates, relieves, delays onset of, inhibits progression of, reduces severity of, and/or reduces incidence of the same or other symptom, or of a particular disease, disorder, and/or condition, in the subject.

A. Administration to a Subject

The N-terminal modified PEG-TRAIL conjugate may be formulated into various formulations for oral or parenteral administration upon clinical application. The administration of the formulation to a subject delivers a therapeutically effective amount of the N-terminal modified PEG-TRAIL conjugate to cells and tissue.

The desired dosage may be delivered orally or parenterally once a day, or multiple times a day. For example, the desired dosage may be delivered three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations).

1. Dosage Unit

The dosage for a specific patient may vary according to the patient's weight, age, gender, state of health and diet, administration duration, administration routes, excretion rates and severity of illness. Typically, it is possible to administer an effective dosage once every one to two weeks. Also, the dosage may be taken in a single dose or in several divided doses within a daily effective dosage.

The formulations are typically formulated in dosage unit form for ease of administration and uniformity of dosage. It will be understood, however, that the total daily usage of the compositions will be decided by the attending physician within the scope of sound medical judgment. The specific therapeutically effective dose level for any particular subject or organism will depend upon a variety of factors including the disorder being treated and the severity of the disorder; the activity of the specific active agent employed; the specific composition employed; the age, body weight, general health, sex and diet of the subject; the time of administration, route of administration, and rate of excretion of the specific active agent employed; the duration of the treatment; drugs used in combination or coincidental with the specific active agent employed; and like factors well known in the medical arts.

In certain embodiments, dosage units contain the N-terminal modified PEG-TRAIL in amounts ranging from about 0.001 mg/kg to about 100 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day, to obtain the desired therapeutic effect. The desired dosage may be delivered three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations).

2. Effective Dose

The specific therapeutically effective dose level for any particular subject or organism will depend upon a variety of factors including the disorder being treated and the severity of the disorder; the activity of the specific effective agent employed; the specific composition employed; the age, body weight, general health, sex and diet of the subject; the time of administration, route of administration, and rate of excretion of the specific active agent employed; the duration of the treatment; drugs used in combination or coincidental with the specific active agent employed; and like factors well known in the medical arts.

B. Diseases to be Treated

The method includes administering to a subject in need of prophylactic or therapeutic treatment the formulation containing an effective dose of the N-terminal modified PEG-TRAIL conjugate as an effective agent.

1. Cancer

The formulations and methods are useful for treating subjects with benign or malignant tumors by delaying or inhibiting the growth of a tumor in a subject, reducing the growth or size of the tumor, inhibiting or reducing metastasis of the tumor, and/or inhibiting or reducing symptoms associated with tumor development or growth.

Malignant tumors which may be treated can be classified according to the embryonic origin of the tissue from which the tumor is derived. Carcinomas are tumors arising from endodermal or ectodermal tissues such as skin or the epithelial lining of internal organs and glands. Sarcomas, which arise less frequently, are derived from mesodermal connective tissues such as bone, fat, and cartilage. The leukemias and lymphomas are malignant tumors of hematopoietic cells of the bone marrow. Leukemias proliferate as single cells, whereas lymphomas tend to grow as tumor masses. Malignant tumors may show up at numerous organs or tissues of the body to establish a cancer.

The proliferative disease is cancer, and preferably includes colon carcinoma, glioma, lung carcinoma, prostate carcinoma, brain tumor, lymphomas, and multiple myeloma.

2. Autoimmune Diseases

In yet another aspect, the disclosure provides a preventive or therapeutic agent containing the N-terminal modified PEG-TRAIL conjugate as the effective agent for preventing or treating an autoimmune disease. The autoimmune disease includes lupus (experimental autoimmune encephalomyelitis), rheumatoid arthritis and type I diabetes.

a. Lupus

Systemic lupus erythematosus (SLE) is an autoimmune disease with a broad spectrum of clinical and immunological abnormalities. The presence of autoantibodies, especially those directed to double stranded DNA, is characteristic of the disease. SLE may affect different organ systems, including the skin, joints, central and peripheral nervous system, kidneys, and liver. The etiology of the disease remains unknown. There is, however, increasing evidence that the presence and accumulation of apoptotic cells play a role in autoimmunity (Hooge et al., *Ann Rheum Dis,* 64:854-858 (2005)).

Increased serum soluble TRAIL concentrations in SLE patients were observed and were found to be disease specific. Levels in patients with inactive disease were more often increased than in patients with active disease.

b. Rheumatoid Arthritis

Rheumatoid arthritis (RA) is a form of arthritis that causes pain, swelling, stiffness and loss of function in joints. It can affect any joint but is common in the wrist and fingers. More women than men get rheumatoid arthritis. The disease may be present for only a short time, or symptoms might come and go. The severe form can last a lifetime.

Rheumatoid arthritis is different from osteoarthritis (OA), the common arthritis that often comes with older age. RA can affect body parts besides joints, such as eyes, mouth and lungs. RA is an autoimmune disease, which means the arthritis results from your immune system attacking body's own tissues.

Patients with rheumatoid arthritis (RA) show elevated TRAIL expression when compared with that in patients with osteoarthritis (OA). The inflammatory environment in the arthritic joints of patients with RA appears to promote TRAIL expression in fibroblast-like synoviocytes (FLS) (Audo et al., *Arthritis and Rheumatism,* 63(4):904-913 (2011)).

c. Type 1 Diabetes

Diabetes, or diabetes mellitus, is due to either the pancreas not producing enough insulin or the cells of the body not responding properly to the insulin produced. There are three main types of diabetes mellitus:

Type 1 Diabetes results from the pancreas' failure to produce enough insulin; this form was previously referred to as "insulin-dependent diabetes mellitus" (IDDM) or "juvenile diabetes", Type 2 Diabetes begins with insulin resistance, a condition in which cells fail to respond to insulin properly. As the disease progresses a lack of insulin may also develop; this form was previously referred to as "non insulin-dependent diabetes mellitus" (NIDDM) or "adult-onset diabetes"; and Gestational diabetes, the third main form, occurs when pregnant women, without a previous history of diabetes, develop a high blood sugar level.

Type 1 diabetes must be managed with insulin injections. People with type 1 diabetes need insulin therapy to survive. Type 1 diabetes is an autoimmune inflammatory disease of the pancreatic islets. In human type 1 diabetes and its rodent models, pancreatic β-cells that produce insulin are selectively destroyed by infiltrating inflammatory cells.

The role of TRAIL in vivo may include inhibiting autoimmune inflammation in the islets of Langerhans. TRAIL may inhibit insulitis and suppresses autoimmune diabetes.

Both T-cells and macrophages are involved in mediating β-cell injury in this disease. TRAIL may regulate diabetes through acting on one or both of these cells. TRAIL also may block DNA synthesis and cell cycle progression of T-cells activated by anti-CD3 antibody. TRAIL may mediate negative selection of thymocytes. Therefore, TRAIL may inhibit diabetic inflammation and autoreactive T-cell activation (Lamhamedi-Cherradi et al., *Diabetes* 52:2274-2278 (2003)).

The present invention will be further understood by reference to the following non-limiting examples.

EXAMPLES

Example 1. Preparation of N-Terminal Modified Peg-Trail Conjugate

Materials and Methods 1-1: Culture of *E. coli* Transformed with TRAIL Gene and Protein Expression.

The truncated form of human TRAIL (hTRAIL) used in this test contained amino acids spanning from arginine-114 to glycine-281 (SEQ ID NO: 2) of the full-length form (1-281) of hTRAIL (SEQ ID NO: 1). The recombinant TRAIL was expressed and produced in *E. coli* BL21 (DE3), and an expression plasmid pET3a was used. An isoleucine zipper (ILz) favoring trimer folding was added to an N-terminus of the recombinant hTRAIL. The recombinant hTRAIL was then tagged with six histidine (6×His) residues at its N-terminal end in order to facilitate isolation and purification.

The transformed *E. coli* was cultured in sterile LB medium at 37° C. with agitation for about 12 hrs in the presence of ampicillin (50 mg/L) for selective culture of a transformant. After the transformed *E. coli* was proliferated for the culturing, isopropyl-beta-D-thiogalactoside (IPTG) was added to the culture medium to induce the expression of *E. coli* genotype. After the agitating incubator and the *E. coli* culture was reduced to 27° C., 1 ml of 1M IPTG solution was added to the culture medium. The cells were further cultured for about 7 hrs with agitation to induce protein expression. The cultured cells were harvested by centrifugation at 5,000 g for 10 min.

1-2: Purification of the Recombinant hTRAIL from *E. coli*.

The recombinant hTRAIL was isolated from the transformed *E. coli* cells harvested in Example 1-1 using a Ni-affinity chromatography. First, the cell pellet obtained by centrifugation was suspended in 20 mM phosphate buffer (pH 7.5), and sonicated to disrupt the cell membrane, thereby releasing TRAIL expressed in *E. coli*. After insoluble cellular substrates were removed through centrifugation at 10,000 rpm for 20 min, the supernatant was slowly passed through a column pre-packed with Ni-NTA resin. The recombinant hTRAIL was selectively bound to the column through the interaction between the six N-terminally tagged histidine residues and chelating nickel ions. The column was washed with phosphate buffer (pH 7.5) and phosphate buffer containing 10 mM and 50 mM imidazole to eliminate impurities, including proteins other than the recombinant hTRAIL. Then, the recombinant hTRAIL bound to the column was eluted with phosphate buffer containing 500 mM imidazole. The TRAIL-containing elution fractions were subjected to ultrafiltration to remove the high concentrations of imidazole. The finally isolated, purified product was placed in 50 mM acetate buffer at a pH of 5.0 with a high purity (98% or higher). The results are given in FIG. 1.

The isolated and purified recombinant hTRAIL and elution fractions obtained from the Ni-NTA column (EX: *E. coli* lysates; UB: non-pegylated TRAIL; washing 1 (w1): washing with 10 mM imidazole-containing phosphate buffer; washing 2 (w2): washing with 50 mM imidazole-containing phosphate buffer) were separated by SDS-PAGE (14% gel). As shown in FIG. 1, the recombinant hTRAIL (ILz-hTRAIL) isolated in Example 1-2 was observed to be eluted at a retention time between 135 and 145 min. The SDS-PAGE result indicated that ILz-hTRAIL was successfully isolated and purified using the Ni-NTA column.

1-3: Synthesis and Isolation of PEG-TRAIL Conjugates

The recombinant hTRAIL prepared in Example 1-2 was diluted at 200 μg/ml in 50 mM acetate buffer (pH 5.0), and was mixed with methoxy polyethylene glycol 5000 propionaldehyde (PEG5k). A reducing agent $NaCNBH_3$ was added to the mixture at a final concentration of 20 mM, and the mixture was allowed to react at 4° C. for about 8 to 12 hrs. PEG5k was added to TRAIL at PEG5k reaction molar ratios of 2.5, 5, 7.5 and 10 in order to prepare an N-terminal modified PEG-TRAIL conjugate. Separately, another N-terminal modified PEG-TRAIL conjugate was prepared using methoxy polyethylene glycol 20000 propionaldehyde.

Results

Figure 2:
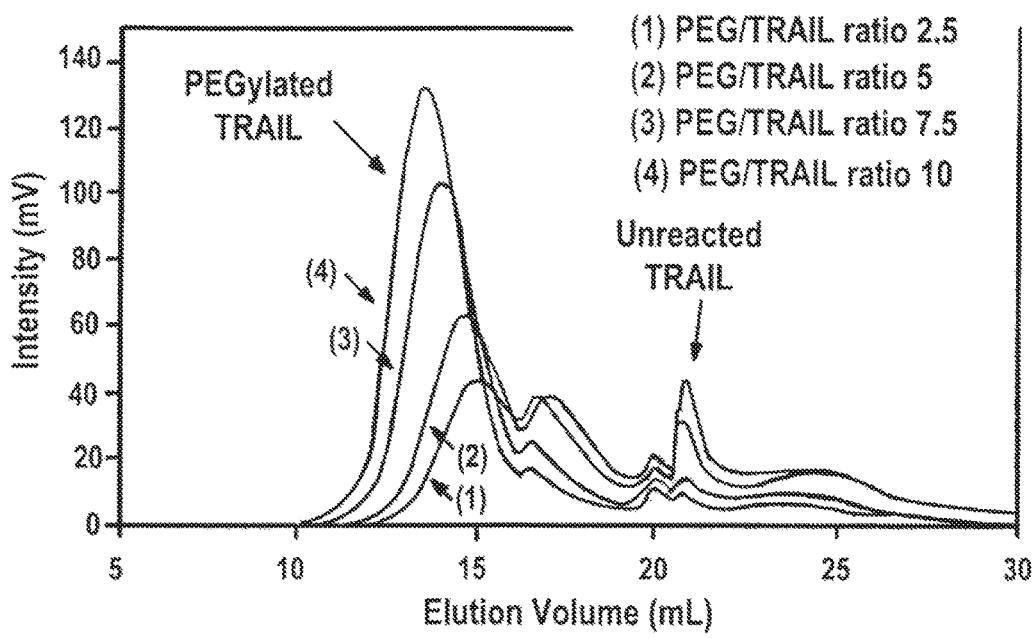
FIG. 2 is a chromatogram showing intensity (mV) as a function of elution volume (ml) for size exclusion chromatography of products formed with various PEG to TRAIL reaction ratios: 1:2.5, 1:5, 1:7.5, and 1:10.

The reaction mixtures were subjected to size exclusion chromatography, and the results are given in FIG. 2. As shown in FIG. 2, the amount of pegylated TRAIL increased with increasing amounts of PEG. However, excessive PEG reacted with side-chain amines of internal lysine residues as well as a desired N-terminal lysine residue, resulting in increased amounts of byproducts. In this case, a resultant conjugate had a higher molecular weight and eluted at an earlier time upon size exclusion chromatography (elution solution: 150 mM NaCl-containing phosphate buffer, pH 6.0). These results indicate that it is effective to set the reaction ratio of PEG to TRAIL within an optimal range so that it is not very high or very low.

An N-terminal modified PEG-TRAIL conjugate, prepared using PEG and TRAIL at a reaction ratio of 7, was isolated and purified through size exclusion chromatography. The results are given in FIG. 3.

Figure 3:
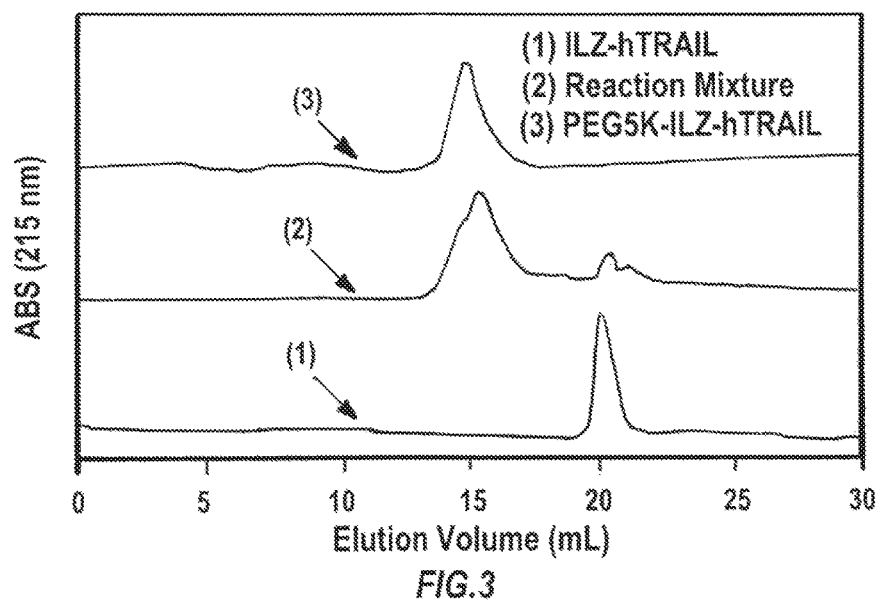
FIG. 3 is a chromatogram showing absorbance at 215 nm as a function of elution volume for (1) ILZ-TRAIL, (2) a reaction mixture, and (3) a purified N-terminal modified PEG-TRAIL conjugate (PEG5K-ILZ-TRAIL).

As shown in FIG. 3, the purified N-terminal modified PEG-TRAIL conjugate was detected at a relatively higher elution volume compared to the non-pegylated recombinant hTRAIL produced in and isolated from *E. coli*. Also, the chromatogram indicated that the purified N-terminal modified PEG-TRAIL conjugate was highly pure and did not contain any unreacted TRAIL.

The purified recombinant hTRAIL and the purified N-terminal modified PEG-TRAIL conjugate were separated by gel electrophoresis. The electrophoresis results showed that compared to the band of monomeric TRAIL, TRAIL monomers were found to exist in the purified N-terminal modified PEG-TRAIL conjugate. This indicates that PEG was bound to the terminal end of one or two monomers of trimeric TRAIL. Also, on the electrophoresis gel, except for monomeric TRAIL and monomers of the N-terminal modified PEG-TRAIL conjugate, no impurities were observed, indicating that the finally purified pegylated TRAIL had a high purity.

Example 2. Comparison of Bioactivity of Non-Pegylated-ILZ-TRAIL and N-Terminal Modified PEG-ILZ-TRAIL Conjugates (Apoptosis Assay)

Materials and Methods

Non-pegylated ILZ-TRAIL and the N-terminal modified PEG-ILZ-TRAIL conjugates were examined for bioactivity, as follows.

An apoptosis assay for the non-pegylated recombinant TRAIL and N-terminal modified PEG-TRAIL conjugates was conducted using human cervical carcinoma HeLa cells and human colon carcinoma HCT116 cells. HeLa cells were cultured in DMEM (Dulbecco's Modified Eagle's Medium), and HCT116 cells in RPMI-1640. Each cell line was seeded onto a 96-well plate at a density of $1\times10^4$ cells/well, and was cultured for about 24 hrs to stabilize it. The cells were dosed with control TRAIL (purchased from R&D systems), the recombinant hTRAIL prepared according to the method of Example 1, and the N-terminal modified PEG-TRAIL conjugates (PEG5K-ILZ-TRAIL and PEG20K-ILZ-TRAIL) at a final concentration of 1 ng/ml to 5 µg/ml for about 24 hrs. Then, 20 µl of MTS solution (Promega) was added to each well, and the plate was incubated for about 2 hrs. Absorbance was measured at 490 nm, and cell viability was calculated from the absorbance. The results are given in FIGS. 4 and 5.

Results

Figure 4:
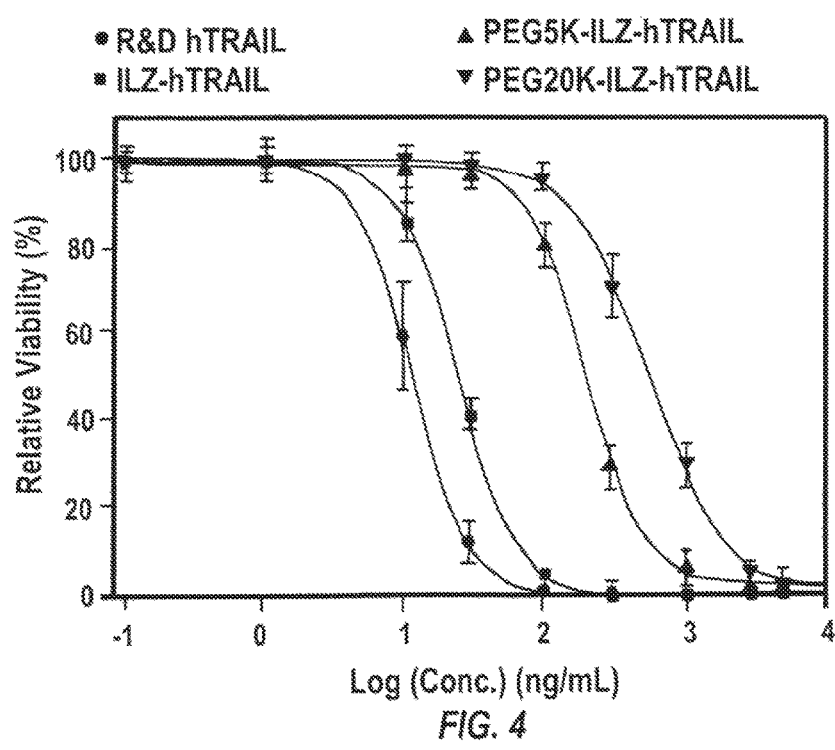
FIG. 4 is a line graph showing the change in relative viability (%) of human cervical carcinoma HeLa cells as a function of concentration (Log. (Conc.) (ng/ml)) of different TRAIL molecules: TRAIL (●), ILZ-TRAIL (■), PEG5K-ILZ-TRAIL (▲), and PEG20K-ILZ-TRAIL (▼).

As shown in FIG. 4, similar to non-pegylated TRAIL, the N-terminal modified PEG-TRAIL conjugates were found to have cytotoxicity against HeLa cells in a dose-dependent manner. The N-terminal modified PEG-TRAIL conjugates were observed to have relatively low cytotoxicity with increasing molecular weight of the attached PEG.

Figure 5:
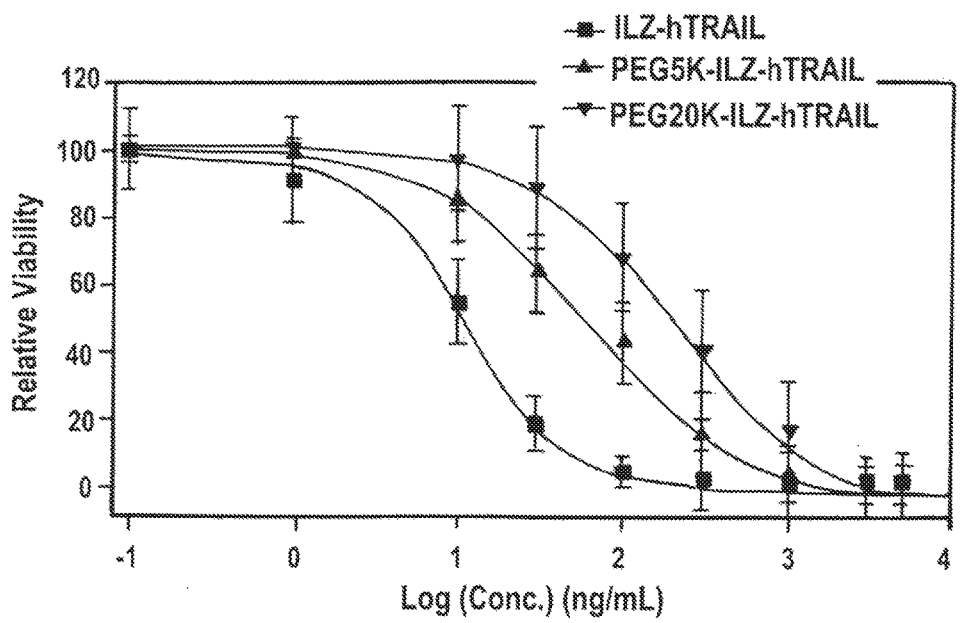
FIG. 5 is a line graph showing the change in relative viability (%) of human colon carcinoma HCT116 cells as a function of concentration (Log. (Conc.) (ng/ml)) of different TRAIL molecules: ILZ-TRAIL (■), PEG5K-ILZ-TRAIL (▲), or PEG20K-ILZ-TRAIL (▼).

As shown in FIG. 5, the PEG-TRAIL conjugates exhibited cytotoxicity against colon carcinoma HCT116 cells in a manner similar to that observed in FIG. 4.

Example 3. Evaluation of Solution Solubility of N-Terminal Modified PEG-TRAIL Conjugates Materials and Methods The non-pegylated recombinant TRAIL and N-terminal modified PEG-TRAIL conjugates were examined for solution stability, as follows.

The solubility of non-pegylated and pegylated TRAIL was assayed over time in order to investigate the solution stability thereof. The non-pegylated TRAIL and N-terminal modified PEG-TRAIL conjugates were individually prepared at 200 µg/ml in 50 mM acetate buffer, diluted at a 1:1 ratio with 100 mM phosphate buffer to adjust the physiological pH value, and then analyzed for solubility over time at 37° C. Samples were collected in small amounts at 5, 15, 30, 60, 120 and 180 min. The collected samples were centrifuged to separate soluble and precipitated fractions. For the soluble fractions thus obtained (as supernatants), protein concentrations were determined using a BCA protein assay kit. The results are given in FIG. 6.

Results

Figure 6:
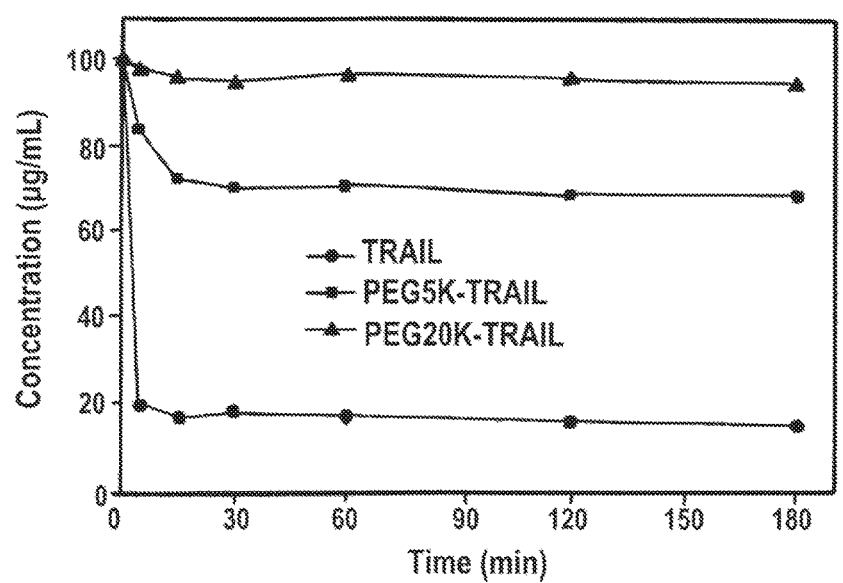
FIG. 6 is a line graph showing the solution solubility and stability of non-pegylated TRAIL (●), and N-terminal modified PEG-TRAIL conjugates PEG5K-ILZ-TRAIL (■), and PEG20K-ILZ-TRAIL (▲) as change in concentration (µg/ml), over time (min).

As shown in FIG. 6, a remarkable difference in solution stability was observed between non-pegylated TRAIL and N-terminal modified PEG-TRAIL conjugates. Most non-pegylated TRAIL (more than 80% thereof) was precipitated within 5 min. In contrast, N-terminal modified PEG-TRAIL conjugates exhibited very high solution stability, and this stability increased with increasing molecular weights of PEG. PEG5K-ILz-hTRAIL displayed a stability of about 70%, and PEG20K-ILz-hTRAIL displayed a stability of about 95%.

Example 4. Evaluation of Pharmacokinetic Profiles of an N-Terminal Modified PEG-TRAIL Conjugate Materials and Methods The non-pegylated TRAIL (ILZ-TRAIL) and N-terminal modified PEG-TRAIL conjugate (PEG5K-ILZ-TRAIL) were examined for pharmacokinetic profiles, as follows.

In order to estimate in vivo behavior of the non-pegylated TRAIL and N-terminal modified PEG-TRAIL conjugate, pharmacokinetic analysis was preformed using 6-week-old Sprague-Dawley rats. In order to facilitate the collection of blood samples from the animal; the right jugular vein of each of the rats was cannulated by inserting one end of a length of PE-10 tubing into the jugular vein about 2.5 cm deep, and suturing it in place. The other end of the tubing was passed through the back of the animal and connected to a blood collection tube at the exterior. The rats were then allowed to acclimatize and recover for about 24 hrs. The non-pegylated TRAIL and N-terminal modified PEG-TRAIL conjugate were subcutaneously administered to the rats at a dosage of 10 µg/kg. Blood samples (0.2 ml each) were collected at given time points for a test period of 48 hrs (the first blood sample was collected at 5 min). After the collected blood samples were centrifuged, the plasma samples were analyzed for in vivo behavior of the non-pegylated TRAIL and N-terminal modified PEG-TRAIL conjugate using a human TRAIL ELISA kit.

Results

Figure 7:
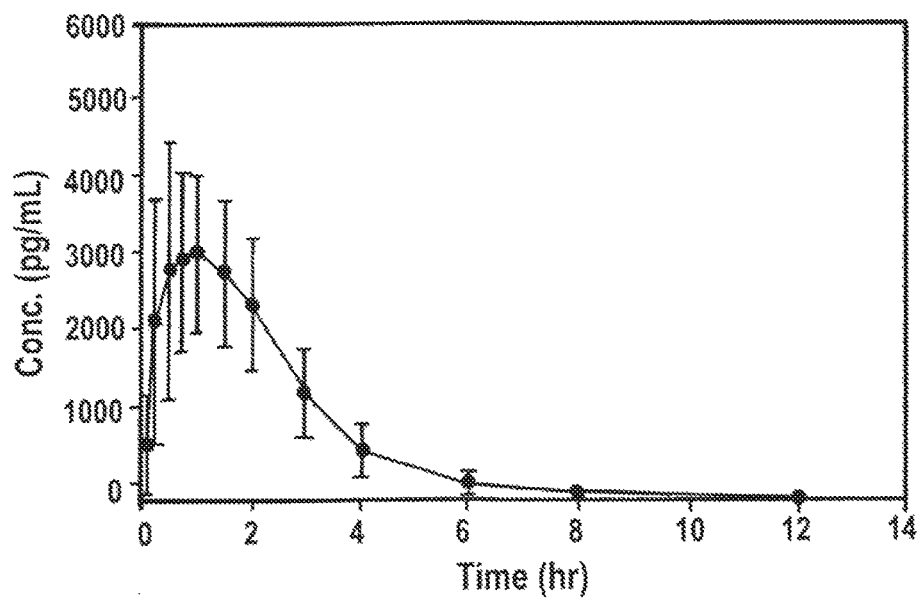
FIG. 7 is a line graph showing the pharmacokinetic profile of non-pegylated ILZ-TRAIL as change in concentration (pg/ml) over time (hr), after subcutaneous administration to rats.
Figure 8:
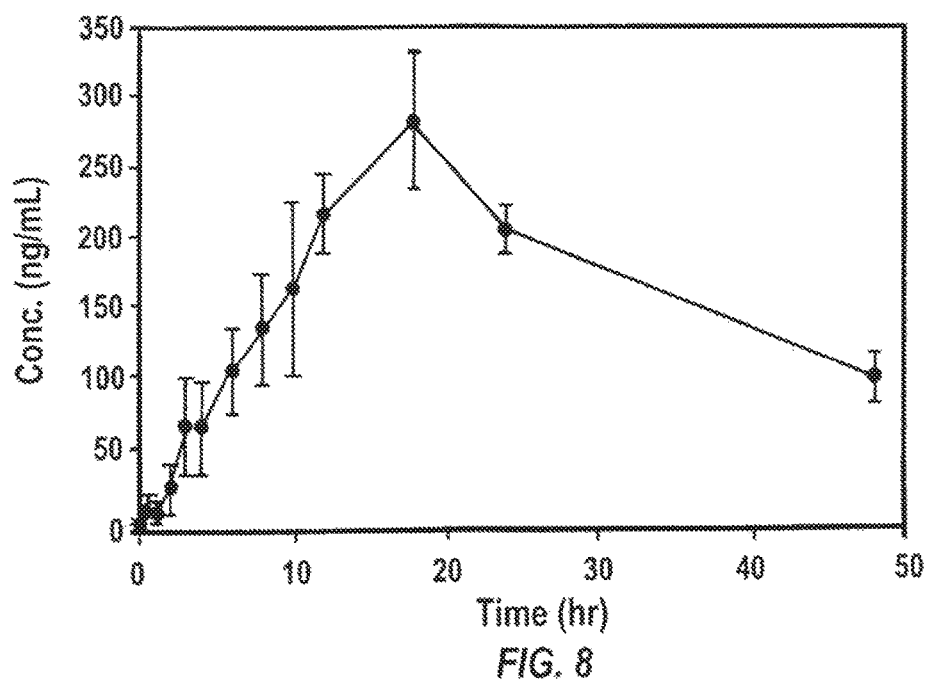
FIG. 8 is a line graph showing the pharmacokinetic profile of an N-terminal modified PEG5K-ILZ-TRAIL conjugate as change in concentration (ng/ml) over time (hr) after subcutaneous administration to rats.

The results are given in FIGS. 7 and 8, respectively. As shown in FIGS. 7 and 8, there was a difference in in vivo behavior between the non-pegylated TRAIL and N-terminal modified PEG-TRAIL conjugate. The non-pegylated TRAIL (ILZ-TRAIL) was rapidly absorbed, and exhibited the highest concentration in the blood after about one hour, but the blood concentration thereof was decreased by rapid renal excretion and metabolization. In contrast, the N-terminal modified PEG-TRAIL conjugate (PEG5K-ILZ-TRAIL) was slowly absorbed from the administered subcutaneous region, and was maintained at high concentrations in the blood for a period of about 48 hrs or longer. This was considered to be due to the low renal excretion and low hepatic metabolization of TRAIL resulting from pegylation.

The results of the pharmacokinetic analysis are given in Table 1.

TABLE 1

Pharmacokinetic profiles of non-pegylated TRAIL
and N-terminal modified PEG-TRAIL conjugate.

|  | ILZ-TRAIL | PEG5K-ILZ-TRAIL |
|---|---|---|
| AUC (ng.hr/ml) | 7.71 ± 1.1 | 7628.2 ± 321.6 |
| Cmax (ng/ml) | 3.38 ± 0.48 | 298.3 ± 24.8 |
| $T_{max}$ (hr) | 0.96 ± 0.19 | 19.0 ± 1.0 |
| $T_{1/2}$ (hr) | 0.79 ± 0.01 | 24.5 ± 4.0 |

As shown in Table 1, compared to ILZ-TRAIL, PEG5K-ILZ-TRAIL existed at higher levels in blood, and had $T_{max}$ (time to reach maximum concentration) more than 19 times higher and $T_{1/2}$ 30 times longer. These results indicate that the N-terminal modified PEG-TRAIL conjugate according to the disclosure is a pharmacokinetically active drug.

Example 5. Preparation of Exemplary Formulations of the PEG-TRAIL Conjugate

Preparation of Pharmaceutical Formulations
Pharmaceutical formulations containing the N-terminal modified PEG-TRAIL conjugate according to the disclosure were prepared as follows.

| 1. Preparation of Powders | |
|---|---|
| N-terminal modified PEG-TRAIL conjugate | 2 g |
| Lactose | 1 g |

The above components were mixed and placed in an airtight pack, thereby giving powders.

| 2. Preparation of Tablets | |
|---|---|
| N-terminal modified PEG-TRAIL conjugate | 100 mg |
| Corn starch | 100 mg |
| Lactose | 100 mg |
| Magnesium stearate | 2 mg |

The above components were mixed and tableted according to a common tablet preparation method, thereby giving tablets.

| 3. Preparation of Capsules | |
|---|---|
| N-terminal modified PEG-TRAIL conjugate | 100 mg |
| Corn starch | 100 mg |
| Lactose | 100 mg |
| Magnesium stearate | 2 mg |

The above components were mixed and loaded into gelatin capsules according to a common capsule preparation method, thereby giving capsules.

| 4. Preparation of Injectable Solution | |
|---|---|
| N-terminal modified PEG-TRAIL conjugate | 10 μg/ml |
| Dilute hydrochloric acid BP | up to pH 3.5 |
| Injectable sodium chloride BP | maximum 1 ml |

The N-terminal modified PEG-TRAIL conjugate was dissolved in a suitable volume of injectable sodium chloride BP, and was adjusted to a pH of 3.5 using dilute hydrochloric acid BP. Injectable sodium chloride BP was further added to achieve a desired volume, and the solution was sufficiently mixed. The mixture solution was then filled into a 5-ml type I ampule made of transparent glass. The glass was melted to seal the ampule, which was autoclaved at 120° C. for 15 min, thereby giving an injectable solution.

Example 6. Preparation of Mono-PEGylated TRAIL Conjugates

Through MALDI mass analysis, it was found that N-terminal PEGylated-ILZ-TRAIL, conjugated with 5,000 Da PEG, purified by SEC is composed of a mixture of trimeric TRAIL conjugated with one, two and/or three PEGs on the N-terminal region. Although N-terminal PEGylated TRAIL retains significantly higher activity compared to randomly PEGylated TRAIL, each isomer (mono-, di-, and/or tri-PEGylated TRAIL) may vary in biological activity. Therefore, one cannot control or predict the properties of the mixture completely. Mono-PEGylated proteins can be separated from those containing larger numbers of PEG or non-PEGylated proteins by SEC, though it is very difficult to purify different PEGylated isomers with similar molecular weights. For example, N-terminal PEGylated trimeric TRAIL isomers with different numbers of 5,000 Da PEG molecules have similar overall molecular weights and thus exhibit one peak in SEC spectra.

Figure 9A:
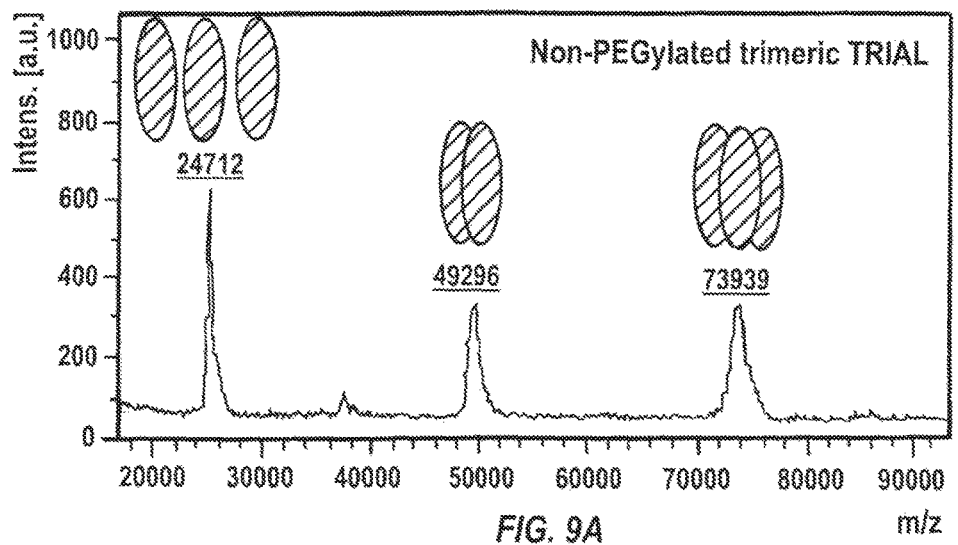
FIGS. 9A and 9B are MALDI-TOF mass spectrums of unpegylated ILZ-TRAIL (9A) or N-terminal mono-PEGylated trimeric ILZ-TRAIL purified by cation exchange chromatography (9B). Molecules corresponding to each of the peaks in the spectrum are schematically shown, and represent a TRAIL monomer (shaded oval), or a TRAIL monomer PEGylated with one molecule of PEG (shaded oval with a tail).
Figure 9B:
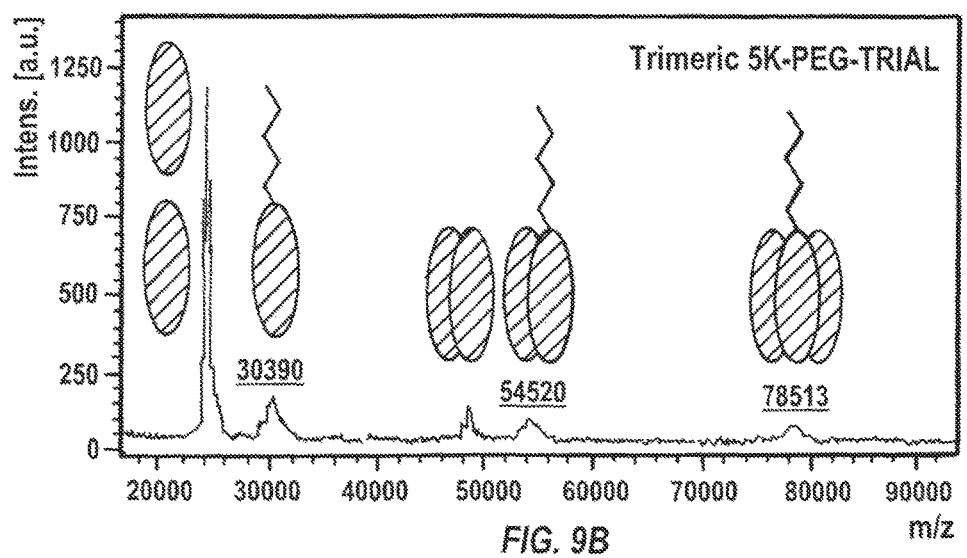
Figure 10:
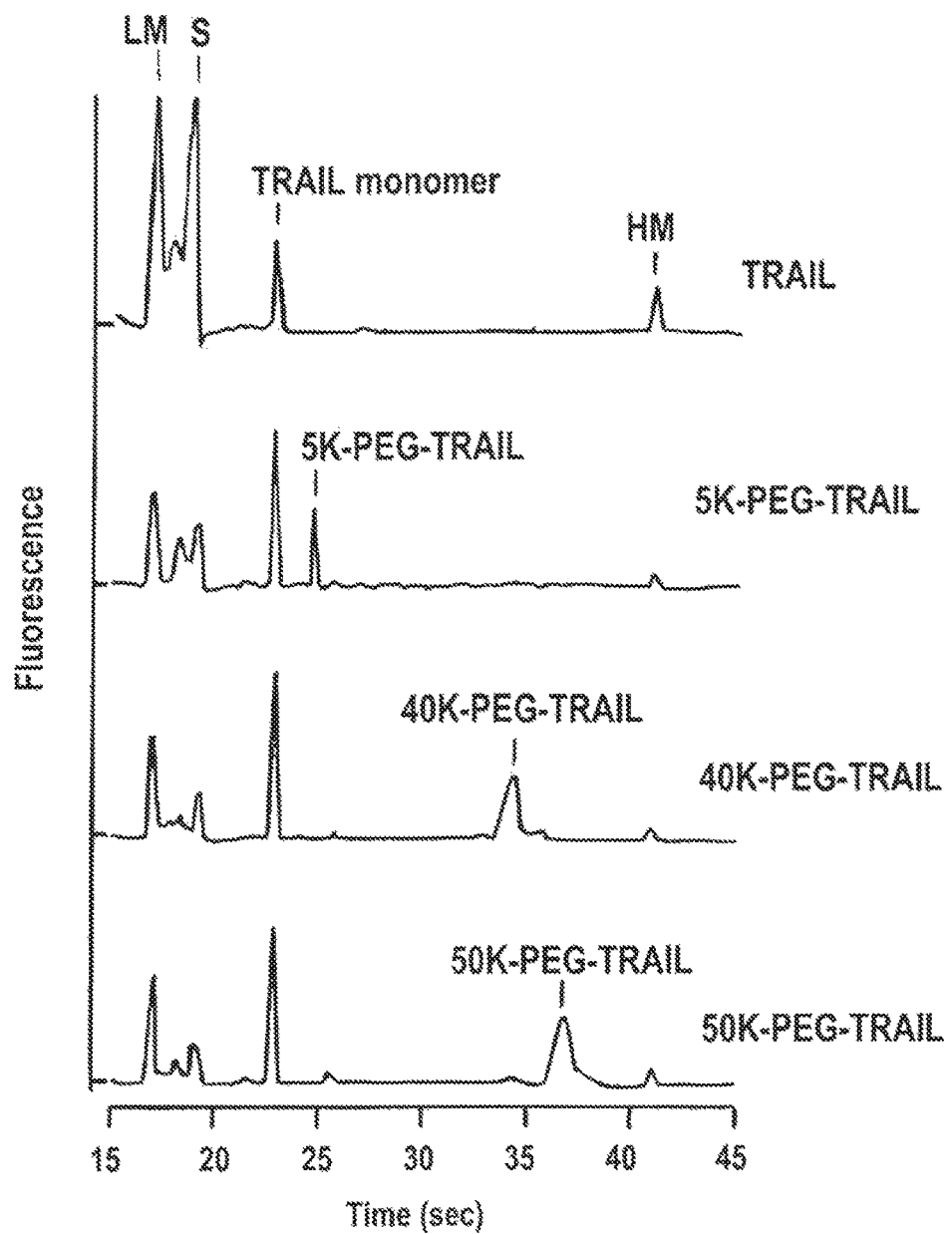
FIG. 10 is a microchip electrophoresis electropherogram of TRAIL or PEGylated TRAIL conjugated with either 5 kDa, 40 kDa, or 50 kDa PEG, and purified by cation exchange chromatography. LM: low MW marker, HM: high MW marker, S: system peak.

This example provides a method of producing only mono-PEGylated trimeric TRAIL by restricting PEG to protein ratios in the reaction and utilizing ion exchange chromatography (IEX). N-terminal PEGylated TRAIL can be obtained by the method described in Example 1. Unlike the SEC method, the purification method using cation exchange chromatography provides highly pure N-terminal, mono-PEGylated trimeric TRAIL in a single chromatographic step as evidenced by MALDI mass analysis (FIGS. 9A and 9B) and microchip electrophoresis (FIG. 10).

Materials and Methods
Synthesis of Mono PEGylated TRAIL Conjugates
PEGylated TRAIL conjugates were prepared as described in Example 1 above with various molecular weights of PEG. Purified trimer ILZ-TRAIL was PEGylated in an N-terminal specific manner. PEG-aldehyde with molecular weight of 5, 10, 20, 40, and 50 kDa (5-20 kDa PEG-aldehyde were linear, 40 kDa was PEG-aldehyde branch, and 50 kDa PEG-aldehyde was trimeric) was purchased from Nippon Oil and Fats (NOF, Tokyo, Japan). PEGylated TRAIL analogs were prepared using PEG-aldehyde (5, 10, 20, 40 and 50 kDa) in the presence of 20 mM sodium cyanoborohydride ($NaCNBH_3$) in 50 mM sodium acetate buffer at pH 5. The protein:PEG molar ratios and the reaction time were varied from 1:1 to 1:10 and from 4 hours to 48 hours. After the reaction, the reaction mixtures were concentrated by ultrafiltration followed by ion exchange chromatography.

Purification of the Conjugates
Each PEGylated TRAIL conjugate was purified by cation exchange chromatography at the conditions described below:

(a) load solution: Buffer exchanged PEGylated TRAIL more than 95%. pH value in load is ca. 7. PEGylated TRAIL concentration is ca. 1 mg/mL;

(b) column: HiTrap SPFF;

(c) buffers, Equilibration buffer: 20 mM phosphate buffer, pH 7. Elution buffer: 1M NaCl. Linear gradient from 100% equilibration buffer to 70% Elution buffer; and (d) Isolated PEGylated TRAIL conjugates were analyzed by MALDI mass, microchip electrophoresis (Agilent 2100 Bioanalyzer) and SDS-PAGE.

Results

The results of the chromatographic purification are shown in FIG. 9. Compared to PEGylated TRAIL purified by size exclusion chromatography (SEC) method, ion exchange (IEX) purification method demonstrated that the product was a mono-PEGylated trimer TRAIL and separated from mixtures of PEGylated isomers. Purified PEGylated TRAIL conjugates were further analyzed by microchip electrophoresis. Representative electropherograms are shown in FIG. 9 and demonstrate that PEGylated trimeric TRAIL includes non-PEGylated TRAIL monomers and PEGylated TRAIL monomers. Combined with the MALDI mass analysis, the efficient purification method confirms that the purified product is mono-PEGylated trimeric TRAIL, and not a mix of mono-, di-, or tri-PEGylated TRAIL. The calculated purity was >90% There was no unpegylated TRAIL.

Example 7. Potency of N-Terminal Modified PEG-TRAIL Conjugate Purified by Ion Exchange Compared to Size Exclusion Chromatography Materials and Methods The in vitro cytotoxicities of PEGylated TRAIL conjugates were determined by cell death MTT assays using human colon tumor cells, HCT116. For comparison, TRAIL was randomly PEGylated with PEG-NETS (5, 10, 20, 40 and 50 kDa) and purified by SEC as described above. The cells were maintained in DMEM supplemented with 10% FBS containing 1% penicillin and streptomycin. For dose-dependent cytotoxicity assays, cells were seeded in 96 well plates at $1 \times 10^4$ cells per well and preincubated for 24 hours. After preincubation, various concentrations of PEGylated TRAIL analogs were added to final concentrations of 0, 10, 30, 100, 300, 1,000 ng/mL. The activities of PEGylated TRAIL were determined by performing MTT assays after incubation for 24 hours. IC50 values were analyzed using GraphPad Prism 6 software. Differences between two means were assessed by a paired or unpaired t-test. Probabilities of $P<0.05$ or as indicated were considered statistically significant.

Results

The results are summarized in Table 2. The data show that PEGylated TRAIL conjugates purified by IEX remained biologically active and exhibited more than 10-fold greater potency (more than 10-lower IC50) than the PEGylated TRAILs purified by SEC method.

TABLE 2

Biological activities of N-terminal PEGylated-ILZ-TRAIL conjugates purified by SEC and IEX methods and randomly PEGylated ILZ-TRAIL conjugates.

| | IC50 (ng/mL) | |
|---|---|---|
| | Purified by SEC* | Purified by IEX |
| N-terminal PEGylation | | |
| PEG-TRAIL, 5 kDa PEG | 69.6 | 7.9 |
| PEG-TRAIL, 10 kDa PEG | 170.3 | 15.5 |
| PEG-TRAIL, 20 kDa PEG | 229.2 | 19.3 |
| PEG-TRAIL, 30 kDa PEG | 494.7 | 25 |
| PEG-TRAIL, 40 kDa PEG | | 28.9 |
| PEG-TRAIL, 50 kDa PEG | | 24.4 |
| Random PEGylation | | |
| PEG-TRAIL, 5 kDa PEG | >1,000 | |
| PEG-TRAIL, 10 kDa PEG | >1,000 | |

TABLE 2-continued

Biological activities of N-terminal PEGylated-ILZ-TRAIL conjugates purified by SEC and IEX methods and randomly PEGylated ILZ-TRAIL conjugates.

| | IC50 (ng/mL) | |
|---|---|---|
| | Purified by SEC* | Purified by IEX |
| PEG-TRAIL, 20 kDa PEG | >1,000 | |
| PEG-TRAIL, 30 kDa PEG | >1,000 | |
| PEG-TRAIL, 40 kDa PEG | >1,000 | |
| PEG-TRAIL, 50 kDa PEG | >1,000 | |

*reported values from Kim et al., Bioconjug. Chem., 22: 1631-1637 (2011)

After the N-terminal PEGylated TRAIL analogs were purified using an optimized IEX purification strategy, the PEG-TRAIL analogs had higher in vitro bioactivity than the SEC-purified PEG-TRAIL based on the same cytotoxicity studies in HCT 116 cells. For example, IEX purified PEG-TRAIL, N-terminally PEGylated with high molecular weights, such as 40 kDa and 50 kDa, demonstrated increased activity compared to that of SEC purified N-terminal PEGylated TRAIL with 5 kDa PEG (Table 2). Randomly PEGylated TRAIL molecules showed significantly reduced biological activity compared to that of N-terminal PEGylated TRAIL analogs.

Example 8. Toxicity Testing of N-Terminal Modified PEG-ILZ-TRAIL with Primary Hepatocytes Materials and Methods To investigate potential liver toxicity, primary human hepatocytes were treated in vitro with varying concentrations of PEGylated and non-PEGylated His-ILZ-TRAIL. Cryopreserved human primary hepatocytes, human hepatocyte plating medium, and thawing medium were obtained from TRL (Triangle Research Labs, LLC, Durham, N.C.). According to the manufacturer's instructions, cryopreserved hepatocytes were thawed in thawing medium and cultured in human hepatocyte plating medium in a 6-well plate of collagen type I Biocoat (BD Biosciences, San Jose, Calif.). Cells were cultured overnight and then treated with various concentrations (0-5,000 ng/mL) of PEGylated TRAIL or non-PEGylated His-ILZ-TRAIL, or Control, Ctrl (buffer only), for 3 hours. Cell viability was analyzed by MTT assays.

Results

Figure 11:
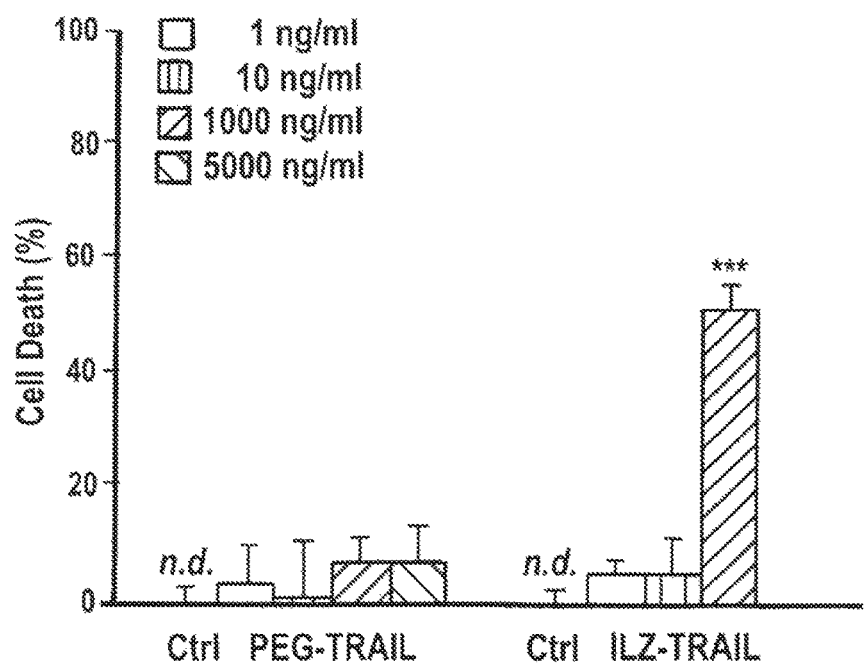
FIG. 11 is a bar graph showing percentage of cell death (%) of primary human hepatocytes following treatment with PEG-ILZ-TRAIL or ILZ-TRAIL (1 µg/mL). Data expressed as mean±s.d. *$P<0.001$ vs. non-treated groups. n.d. none detected.

FIG. 11 shows that PEGylated TRAIL is non-toxic to hepatocytes when compared to His-tagged ILZ-TRAIL. At concentrations higher than 1,000 ng/mL, His-ILzZ-TRAIL induced apoptosis in human hepatocytes in vitro. In contrast, PEGylated TRAIL did not show toxicity with any of the tested concentrations (1, 10, 1000 and 5,000 ng/mL).

Recombinant native-type TRAIL is known to be non-toxic to primary hepatocytes, which express the death receptors TRAIL-R1/DR4 and TRAIL-R2/DR5. These cells are resistant to TRAIL-induced apoptosis (Lawrence et al., Nat Med, 7(4):383-385 (2001)). However, some TRAIL variants, including His-tagged or Flag-tagged TRAIL have been found to be hepatotoxic (Ganten et al., Clin Cancer Res, 12(8):2640-2646 (2006)). It has been reported that such tags can induce uncontrolled TRAIL aggregation that induce strong apoptosis in hepatocytes and can lead to liver toxicity. As shown in FIG. 11, the His-tagged ILZ-TRAIL induced apoptosis in human hepatocytes at concentrations above 1,000 ng/mL. In contrast, PEGylated-ILZ-TRAIL did not show toxicity at concentrations of up to 5,000 ng/mL.

PEG-TRAIL conjugates purified both by SEC and IEX did not show any toxicity in hepatocytes.

Example 9. Assessing Anti-Cancer Activity of N-Terminal Modified PEG-ILZ-TRAIL Compared to Randomly PEGylated-ILZ-TRAIL in Tumor Xenografts Materials and Methods HCT116 human colon cancer cells were maintained in RPMI 1640 medium supplemented with 10% fetal bovine serum, 1% penicillin, and 1% streptomycin. Cells were cultured at 37° C. under an atmosphere of 5% $CO_2$. PC3 human prostate cancer cells were maintained in F-12K medium (Sigma) supplemented with 10% FBS, 1% penicillin, and 1% streptomycin. The cell lines were purchased from ATCC (Manassa, Va.).

Freshly harvested HCT116 cells ($3 \times 10^6$ cells per mouse) were inoculated s.c. into BALB/c athymic mice (n=5 per group). When tumor volume reached ~200 mm$^3$, mice were i.v. treated with N-terminal modified PEG5K-ILZ-TRAIL (N-term PEG-TRAIL, 10 mg/kg), randomly PEGylated PEG5K-ILZ-TRAIL (random PEG-TRAIL, 10 mg/kg) or vehicle (PBS) daily for 10 days For PC3 models, freshly harvested PC3 cells ($10^6$ cells per mouse) were inoculated s.c. into BALB/c athymic mice (n=6 per group). Treatment was initiated when tumors reached a volume of ~200 mm$^3$. Mice were i.v. treated with N-terminal modified PEG5K-ILZ-TRAIL (N-term, PEG-TRAIL, 10 mg/kg), randomly PEGylated PEG5K-ILZ-TRAIL (random PEG-TRAIL, 10 mg/kg) or vehicle (PBS) daily for 10 days.

Tumor volumes were monitored after tumor cell administration. Tumor volumes were calculated using longitudinal (L) and transverse (W) diameters using $V=(L \times W^2)/2$. At the end of treatment, tumor tissues were isolated from euthanized animals. Sections (5 micrometers) were cut from 10% neutral buffered, formalin-fixed, paraffin-embedded tissue blocks. All data were analyzed by GraphPad Prism 6 (GraphPad Software, CA). Differences between two means were assessed by a paired or unpaired t-test. P values <0.05 were considered to be significant.

Results

Figure 12:
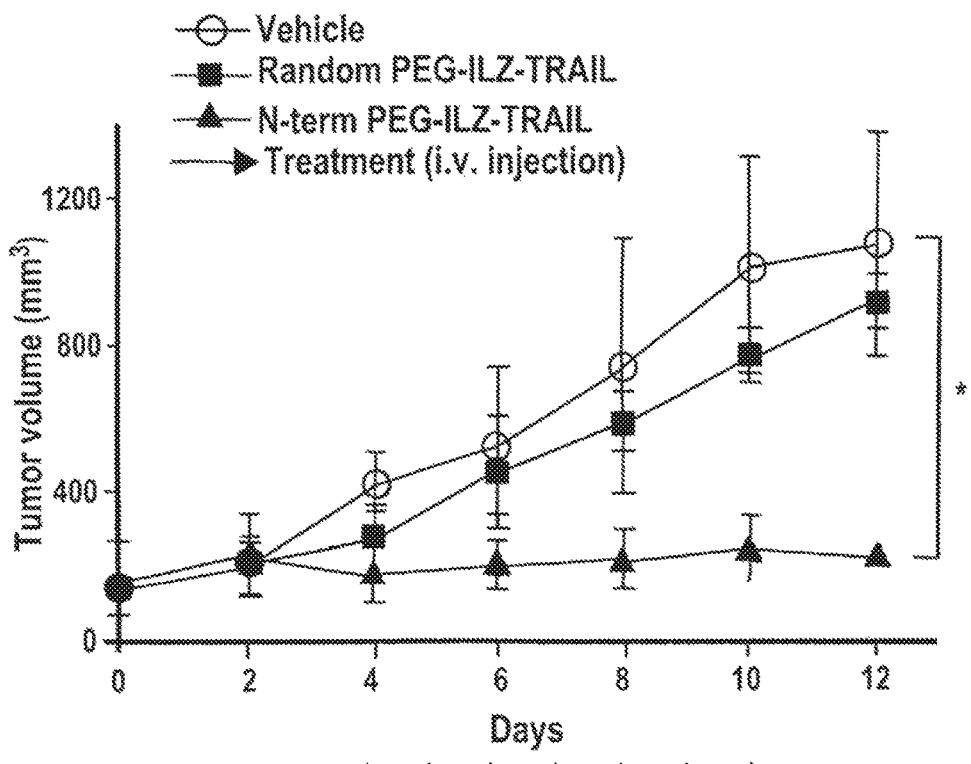
FIG. 12 is a line graph showing the anti-cancer efficacies of TRAIL analogs following intravenous treatment of HCT116 (n=5/group) with N-terminal modified PEG5K-ILZ-TRAIL (N-term PEG-TRAIL), randomly PEGylated PEG5K-ILZ-TRAIL (random PEG-TRAIL) and vehicle. All doses are 10 mg/kg based on TRAIL. Data expressed as mean±s.e.m. *$P<0.05$ for vehicle vs. random PEG5K-ILZ-TRAIL.
Figure 13:
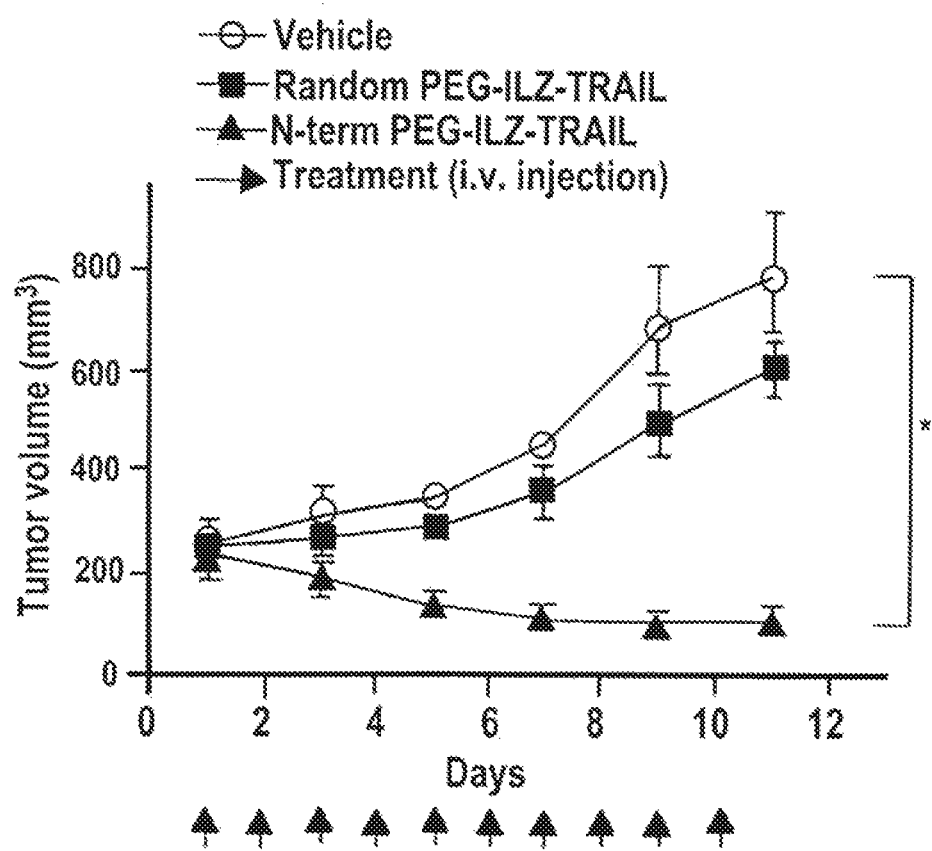
FIG. 13 is a line graph showing the anti-cancer efficacies of TRAIL analogs following intravenous treatment of PC3 xenografts (n=6/group) with N-terminal modified PEG5K-ILZ-TRAIL (N-term PEG-TRAIL), randomly PEGylated PEG5K-ILZ-TRAIL (random PEG-TRAIL) and vehicle. All doses are 10 mg/kg based on TRAIL. Data expressed as mean±s.e.m. *P<0.05 for vehicle vs. random PEG5K-ILZ-TRAIL.

In vivo anti-cancer efficacy studies revealed that HCT116 and PC3 tumor cell growth were significantly inhibited by N-terminal modified PEG5K-ILZ-TRAIL and not by randomly PEGylated PEG5K-ILZ-TRAIL or vehicle alone. HCT116 and PC3 results are summarized in Tables 3 and 4, respectively. Representative tumor growth curve of HCT116 and PC3 xenografts are shown in FIGS. 12 and 13, respectively. Randomly PEGylated TRAIL marginally altered tumor growth as demonstrated in vitro studies. In contrast, N-terminal modified PEG-TRAIL suppressed tumor growth significantly compared to vehicle and randomly PEGylated TRAIL. Combined with our in vitro results described in Example 3, N-terminal modified PEG-ILZ-TRAIL retains superior activity in vitro and in vivo compared to randomly PEGylated-ILZ-TRAIL analogs.

TABLE 3

Tumor volume (mm$^3$) measurements of HCT116 xenografts (n = 5/group) from FIG. 13A.

| Days Post 1$^{st}$ Treatment | Vehicle | | Random-PEG-TRAIL | | N-term-PEG-TRAIL | |
|---|---|---|---|---|---|---|
| | Average | ±SEM | Average | ±SEM | Average | ±SEM |
| 0 | 149.15 | 38.07 | 147.44 | 37.51 | 164.82 | 97.34 |
| 2 | 198.77 | 65.81 | 203.75 | 45.00 | 236.97 | 98.44 |
| 4 | 425.66 | 74.83 | 281.70 | 73.68 | 186.20 | 87.87 |
| 6 | 515.34 | 219.59 | 465.05 | 128.42 | 203.14 | 65.07 |
| 8 | 732.47 | 346.77 | 587.01 | 73.82 | 213.10 | 79.12 |
| 10 | 1006.87 | 294.90 | 764.85 | 70.49 | 248.76 | 90.36 |
| 12 | 1064.47 | 299.45 | 912.97 | 71.45 | 220.38 | 22.01 |

TABLE 4

Tumor volume (mm$^3$) measurements of PC3 xenografts (n = 6/group) from FIG. 13B.

| Days Post 1$^{st}$ Treatment | Vehicle | | Random-PEG-TRAIL | | N-term-PEG-TRAIL | |
|---|---|---|---|---|---|---|
| | Average | ±SEM | Average | ±SEM | Average | ±SEM |
| 1 | 262.90 | 42.65 | 250.97 | 20.07 | 233.80 | 28.67 |
| 3 | 309.78 | 53.17 | 266.77 | 31.22 | 197.30 | 30.26 |
| 5 | 336.93 | 25.26 | 287.48 | 18.27 | 135.15 | 27.19 |
| 7 | 444.53 | 22.88 | 355.14 | 51.34 | 108.28 | 25.44 |
| 9 | 687.80 | 110.31 | 493.94 | 69.56 | 104.77 | 30.19 |
| 11 | 780.11 | 127.37 | 601.11 | 62.15 | 102.95 | 25.59 |

Modifications and variations will be apparent from the foregoing detailed description and are intended to come within the scope of the following claims. All references cited herein are specifically incorporated by reference.

We claim:

1. A method for treating a disease in a subject comprising administering a pharmaceutically effective amount of a polyethylene glycol-tumor necrosis factor-related apoptosis-inducing ligand (PEG-TRAIL) consisting of
a trimeric TRAIL comprising three TRAIL monomers each having the sequence of full length human TRAIL or truncated human TRAIL comprising amino acids 114-281 of full length human TRAIL, the N-terminus of each monomer comprising a zipper amino acid motif, having a PEG or PEG derivative bound to the N-terminus of one of the monomers, wherein the N-terminal modified PEG-TRAIL is purified by ion exchange chromatography to remove any TRAIL monomers or PEG that is not bound to the trimeric TRAIL,
to the subject in need thereof having cancer, an immune or inflammatory disorder, or diabetes.

2. The method of claim 1, wherein the cancer is selected from the group consisting of colon carcinoma, glioma, lung carcinoma, prostate carcinoma, brain tumor, and multiple myeloma.

3. The method of claim 1, comprising administering a pharmaceutically effective amount of the N-terminal modified PEG-TRAIL to a subject having an immune or inflammatory disorder.

4. The method of claim 3, wherein the immune disorder is selected from the group consisting of systemic lupus erythematosus, rheumatoid arthritis, and type I diabetes.

5. The method of claim 1, wherein an effective amount is administered once every one or two weeks.

6. The method of claim 1, wherein the effective amount is administered in a single dose or in several divided doses.

7. The method of claim 1, wherein the subject excretes less of the N-terminal modified PEG-TRAIL in the urine as compared to non-PEGylated TRAIL.

8. The method of claim 1, wherein the N-terminal modified PEG-TRAIL has a decreased protein degradation by proteases when compared to non-PEGylated TRAIL.

9. The method of claim 1, wherein the effective amount is administered orally or parenterally.

10. The method of claim 1, wherein the PEG derivative is selected from the group consisting of methoxypolyethylene glycol succinimidyl propionate, methoxypolyethylene glycol N-hydroxysuccinimide, methoxypolyethylene glycol aldehyde, methoxypolyethylene glycol maleimide, and multiple-branched polyethylene glycol.

11. The method of claim 1 wherein the TRAIL monomers have the amino acid sequence of SEQ ID NO:1 or SEQ ID NO:2.

* * * * *

UNITED STATES PATENT AND TRADEMARK OFFICE
CERTIFICATE OF CORRECTION

PATENT NO. : 10,046,059 B2  
APPLICATION NO. : 15/138109  
DATED : August 14, 2018  
INVENTOR(S) : Kang Choon Lee, Seulki Lee and Eun Ji Park Page 1 of 2

It is certified that error appears in the above-identified patent and that said Letters Patent is hereby corrected as shown below:

On the Title Page

Item (57) Abstract, replace "PEG-TAIL" with --PEG-TRAIL--.
Item (57) Abstract, replace "conjugates exhibits" with --conjugates exhibit--.

In the Specification

Column 2, Line 30, replace "Seol reported" with --Kim reported--.
Column 8, Line 11, replace "4,917,888 describes" with --4,917,888 describe--.
Column 8, Lines 41 and 42, replace "proteins such as hyaluronic acid" with --hyaluronic acid--.
Column 10, Lines 49 and 50, replace "proteins such as hyaluronic acid" with --hyaluronic acid--.
Column 10, Line 51, replace "cellulose, polyvinyl alcohol, and" with --cellulose, and--.
Column 10, Line 55, replace "such as found" with --such as those found--.
Column 10, Line 57, replace "amines. (Molineux" with --amines (Molineux--.
Column 10, Line 59, replace "such as found" with --such as those found--.
Column 11, Line 8, replace "acylic" with --acrylic--.
Column 11, Lines 52 and 53, replace "auxiliaries which facilitate" with
--auxiliaries, which facilitate--.
Column 11, Line 61, replace "included with the insulin to promote" with --included to promote--.
Column 12, Line 8, replace "(or glycerin, or glycerin)" with --(or glycerin, or glycerine)--.
Column 12, Lines 12 and 13, replace "soya bean" with --soybean--.
Column 12, Line 40, replace "sensitizers includes, but is not limited" with --sensitizers include, but are not limited--.
Column 14, Line 41, replace "in need thereof." with --in need thereof are provided.--.
Column 14, Line 47, replace "disease is when" with --disease when--.
Column 17, Line 56, replace "culture was reduced" with --culture, the temperature was reduced--.
Column 22, Line 38, replace "Mono PEGylated" with --Mono-PEGylated--.
Column 23, Line 3, replace "FIG. 9." with --FIGs. 9A and 9B.--.
Column 23, Line 9, replace "FIG. 9" with --FIGs. 9A and 9B--.
Column 25, Line 26, replace "10 days" with --10 days.--.

Signed and Sealed this  
Second Day of April, 2019

Andrei Iancu  
*Director of the United States Patent and Trademark Office*

Column 26, Table 3, Line 2, replace "FIG. 13A." with --FIG. 12.--.
Column 26, Table 4, Line 2, replace "FIG. 13B." with --FIG. 13.--.

In the Claims

Claim 5, Column 30, Line 13, replace "wherein an effective amount" with --wherein the effective amount--.

SEQUENCE LISTING

```
<160> NUMBER OF SEQ ID NOS: 2

<210> SEQ ID NO 1
<211> LENGTH: 281
<212> TYPE: PRT
<213> ORGANISM: Homo sapiens

<400> SEQUENCE: 1

Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Met Gln Asp Lys
        35                  40                  45
```

```
Tyr Ser Lys Ser Gly Ile Ala Cys Phe Leu Lys Glu Asp Asp Ser Tyr
     50                  55                  60

Trp Asp Pro Asn Asp Glu Glu Ser Met Asn Ser Pro Cys Trp Gln Val
 65                  70                  75                  80

Lys Trp Gln Leu Arg Gln Leu Val Arg Lys Met Ile Leu Arg Thr Ser
                 85                  90                  95

Glu Glu Thr Ile Ser Thr Val Gln Gly Lys Gln Gln Asn Ile Ser Pro
            100                 105                 110

Leu Val Arg Glu Arg Gly Pro Gln Arg Val Ala Ala His Ile Thr Gly
        115                 120                 125

Thr Arg Gly Arg Ser Asn Thr Leu Ser Ser Pro Asn Ser Lys Asn Glu
130                 135                 140

Lys Ala Leu Gly Arg Lys Ile Asn Ser Trp Glu Ser Ser Arg Ser Gly
145                 150                 155                 160

His Ser Phe Leu Ser Asn Leu His Leu Arg Asn Gly Glu Leu Val Ile
                165                 170                 175

His Glu Lys Gly Phe Tyr Tyr Ile Tyr Ser Gln Thr Tyr Phe Arg Phe
            180                 185                 190

Gln Glu Glu Ile Lys Glu Asn Thr Lys Asn Asp Lys Gln Met Val Gln
        195                 200                 205

Tyr Ile Tyr Lys Tyr Thr Ser Tyr Pro Asp Pro Ile Leu Leu Met Lys
210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
                245                 250                 255

Phe Val Ser Val Thr Asn Glu His Leu Ile Asp Met Asp His Glu Ala
            260                 265                 270

Ser Phe Phe Gly Ala Phe Leu Val Gly
        275                 280

<210> SEQ ID NO 2
<211> LENGTH: 167
<212> TYPE: PRT
<213> ORGANISM: Homo sapiens

<400> SEQUENCE: 2

Arg Glu Arg Gly Pro Gln Arg Val Ala Ala His Ile Thr Gly Thr Arg
 1               5                  10                  15

Gly Arg Ser Asn Thr Leu Ser Ser Pro Asn Ser Lys Asn Glu Lys Ala
                20                  25                  30

Leu Gly Arg Lys Ile Asn Ser Trp Glu Ser Ser Arg Ser Gly His Ser
            35                  40                  45

Phe Leu Ser Asn Leu His Leu Arg Asn Gly Glu Leu Val Ile His Glu
        50                  55                  60

Lys Gly Phe Tyr Tyr Ile Tyr Ser Gln Thr Tyr Phe Arg Phe Gln Glu
 65                  70                  75                  80

Glu Ile Lys Glu Asn Thr Lys Asn Asp Lys Gln Met Val Gln Tyr Ile
                 85                  90                  95

Tyr Lys Tyr Thr Ser Tyr Pro Asp Pro Ile Leu Leu Met Lys Ser Ala
            100                 105                 110

Arg Asn Ser Cys Trp Ser Lys Asp Ala Glu Tyr Gly Leu Tyr Ser Ile
        115                 120                 125

Tyr Gln Gly Gly Ile Phe Glu Leu Lys Glu Asn Asp Arg Ile Phe Val
130                 135                 140
```

```
Ser Val Thr Asn Glu His Leu Ile Asp Met Asp His Glu Ala Ser Phe
145                 150                 155                 160

Phe Gly Ala Phe Leu Val Gly
                165
```